(12) United States Patent
Wang et al.

(10) Patent No.: US 6,982,323 B1
(45) Date of Patent: Jan. 3, 2006

(54) CHIMERIC PROTEINS FOR DIAGNOSIS AND TREATMENT OF DIABETES

(75) Inventors: Yi Wang, Orange, CT (US); John Mueller, Old Lyme, CT (US); Louis A. Matis, Southport, CT (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 0 days.

(21) Appl. No.: 09/528,225

(22) Filed: Mar. 21, 2000

Related U.S. Application Data

(63) Continuation of application No. PCT/US98/27408, filed on Dec. 23, 1998.
(60) Provisional application No. 60/068,648, filed on Dec. 23, 1997.

(51) Int. Cl.
*C07K 14/62* (2006.01)
*C07K 14/435* (2006.01)
*A61K 38/17* (2006.01)
*A61K 38/28* (2006.01)
*A61K 38/43* (2006.01)

(52) U.S. Cl. ............... 530/403; 530/303; 530/350; 536/23.4; 514/3; 514/866
(58) Field of Classification Search ............... 536/23.4; 530/403, 350; 514/866, 3
See application file for complete search history.

(56) References Cited

U.S. PATENT DOCUMENTS 5,821,334 A * 10/1998 Powers ............... 530/350

OTHER PUBLICATIONS

Ramiya et al. J. Autoimmunity. 10: 287–292, 1997.*
Falorni et al. Diabetologia. 39: 1091–1098, 1996.*
Ammerer, 1983. Meth Enzymol 101:192.
Atkinson and Maclaren, 1993 J Clin Invest 92:1608–1616.
Atkinson et al. 1990 Lancet 335:1357–1360.
Atkinson et al. 1990 Diabetes 39:933–937.
Atkinson et al. 1992 Lancet 339: 458–459.
Atkinson et al. 1993 J Clin Invest 91:350–356.
Baekkeskov et al. 1982 Nature 298:167–169.
Bekkeskov et al. 1987 J Clin Invest 79:926–934.
Baekkeskov et al. 1990 Nature 347:151–156.
Bock et al. 1992 Lancet 339:1504–1506.
Bonifacio et al. 1990 Lancet 335:147–149.
Bowman et al. 1994 Immunol Today 15 (3) :115–120.
Brunner et al. 1995 Nature 373:441–444.
Butler et al. 1993 J Exp Med 178:2097–2106.
Cohen et al. 1992 Ann Rev Immunol 10:267 et seq.
Conrad et al. 1994 Nature 371:351–355.
Cotter et al. 1990 Anticancer Research 10:1153 et seq.
Crispe 1994 Immunity 1:347–349.
Daniel et al. Proc Natl. Acad. Sci. USA 93:956–960.
De Aizpurua et al. 1992 Proc Natl Acad Scie USA 89:9841–9845.
Dhein et al. 1995 Nature 373:438–441.
Evans and Scarpulla 1989 Gene 84:135 et seq.
Garnier et al., 1978 J Mol Biol 120:97–120.
Goeddel et al., 1980 Nucl Acids Res 8:4057 et seq.
Griffin and Griffin, Eds., 1994 PCR Technology, Current Innovations. CRC Press, Boca Raton, FL.
Grosjean and Fiers, 1982 Gene 18:199 et seq.
Hanninen et al., 1992 J Clin Invest 90:1901–1910.
Harrison, 1992 Immunol Today 13:348–352.
Hatfield et al. 1997 Diabetologia 40:1327–1333.
Hernan et al., 1992 Biochemistry 31:8619 et seq.
Herold et al., 1992 J Exp Med 176:1107–1114.
Ho et al. 1989 Gene 77:51–59.
Huang and Gorman, 1990 Mol Cell Biol 10:1805 et seq.
Ju et al. 1995 Nature 373:444–448.
Karjalainen et al., 1992 New Eng J Med 327:302–307.
Kaufman et al., 1993 Nature 366:69–72.
Kawabe and Ochi, 1991 Nature 349:245–248.
Kawaskai et al., 1997 J. Clin. Endocrinol. Metab 82:375–380.
Lenardo, 1991 Nature 353:858–860.
Lohman et al., 1996 J of Autoimmunity 9:385–389.
Lohman et al., 1996 Hormone & Metabolic Res. 28:357–360.
Luckow et al., 1988 Bio/Technology 6:47 et seq.
MacLaren, N and K Laffety 1993 Diabetes 42:1099–1104.
Marrack and Kappler, 1987 Science 238:1073 et seq.
Moir, et al. 1991 Meth Enzymol 194:491–507.
Morgenstern and Land 1990 Nucl Acids Res 18:3587 et seq.
Muir et al., 1995 J Clin Invest 95, pp628–634.
Nagata and Suba, 1995 Immunol Today 16:39 et seq.
Naquet et al., 1988 J Immunol 140:2569–2578.

(Continued)

*Primary Examiner*—Christine J. Saoud
(74) *Attorney, Agent, or Firm*—Wilmer, Cutler, Pickering, Hale and Dorr LLP

(57) ABSTRACT

Novel chimeric fusion proteins comprising immunodominant epitopes of GAD and insulin are provided. Also provided are immunomodulatory methods for the use of such proteins for both the prevention and treatment of Type 1 diabetes mellitus. The chimeric fusion proteins of the invention are useful in predicting risk of onset of Type 1 diabetes, determining prognosis of Type 1 diabetes patients early in disease progression, and in evaluating patients for suitability as recipients of transplants of pancreatic cells or tissues. The administration of the proteins of the invention in accordance with the immunomodulatory methods of the invention results in beneficial effects on disease development and severity in patients suffering from or predicted to be at risk of developing Type 1 diabetes, as well as on the outcome of transplants of pancreatic cells or tissues in Type 1 diabetes patients.

8 Claims, 9 Drawing Sheets

OTHER PUBLICATIONS

Quinn, A and E.E. Sercarz 1996 J Autoimmunity 9:365–370.
Ramiya et al., 1996 J. Autoimmunity 9:349–356.
Richter et al., 1992 Proc Natl Acad Sci USA 89:8467–8471.
Russell et al., 1993 Proc Natl Acad Sci USA 90:4409–4413.
Sato et al., 1994 J Biol Chem 269:17267 et seq.
Schena et al., 1991 Meth Enzymol 194:389–398.
Singer et al., 1994 Immunity 1:365–371.
Solimena and De Camilli, 1993 Nature 366: 15–17.
Steinman, 1995 Cell 80:7–10.
Strasser, 1995 Nature 373:385–386.
Sun et al., Eur J Immunol 21:1461–1468.
Taguchi et al., 1990 J Immunol Meth 128:65–73.
Talib et al., 1991 Gene 98:289–293.
Tisch et al., 1993 Nature 366:72–75.
Von Boehmer, 1988 Ann Rev Immunol 6:309 et seq.
Waslston et al., 1995 N Eng J Med 333:343–347.
Wicker et al., 1996 J Clin Invest 98:2597–2603.
Xie et al., 1997 J Immunol 159:3662–3667.
Zhang et al., 1997 Diabetes 46:40–43.
Zhang et al., 1991 Proc Natl Acad Sci USA 88:10252–10256.
Adorini, L et al. 1993 *Immunol Today* 14:285–289 Selective Immunosuppression.
Allegretta, M et al/1990 *Science* 247:718–722 T Cells Responsive to Myelin basic Protein in Patients with Multiple Sclerosis.
Allegretta, M et al. 1994 *J Clin Invest* 94:105–109 Homologies Between T Cell Receptor Junctional Sequences Unique To Multiple Sclerosis And T Cells Mediating Experimental Allergic Encephalomyelitis.
Alvord, EC et al. 1979 *Ann Neurol* 6:461–468 Has Myelin Basic Protein Received a Fair Trial in the Treatment of Multiple Sclerosis?
Alvord, EC et al. 1979 *Ann Neurol* 6:469–473 Myelin Basic Protein Treatment Of Experimental Allergic Encephalomyelitis in Monkeys.
Amor S, et al. 1994 *Journal of Immunology* 153:4349–4356 Identification of Epitopes of Myelin Oligodendrocyte Glycoprotein for the Induction of Experimental Allergic Encephalomyelitis in SJL and Biozzi AB/H Mice.
Aruga, J et al. 1991 *J Neurochem* 56:1222–1226 Identification of the New Isoforms of Mouse Myelin Basic Protein: The Existence Of Exon 5a.
Boehme, S et al. 1993. *Eur J Immunol* 23:1552–1560 Propriocidal Apoptosis of Mature T Lymphocytes Occurs at S Phase of the Cell Cycle.
Carnegie P, et al. 1971 *Biochem J.* 123:57–67 Amino Acid Sequence of the Encephalitogenic Basic Protein.
Chen, Y et al. 1994 *Science* 265:1237–1240 Regulatory T Cell Clones Induced by Oral Tolerance: Suppression of Autoimmune Encephalomyelitis.
Chou, YK et al. 1991 *J Neurosci Res* 28:280–290 Specificity of Human T Cell Clones Reactive to Immunodominant Epitopes of Myelin Basic Protein.
Correale, J et al. 1995 *J Immunology* 154:2959–2968 Patterns of Cytokine Secretion by Autoreactive Proteolipid Protein–Specific T Cell Clones During the Course of Multiple Sclerosis.
Critchfield, JM et al. 1994 *Science* 263:1139–1143 T Cell Deletion in High Antigen Dose Therapy of Autoimmune Encephalomyelitis.

Diehl H, et al. 1986 *Proc. Natl. Acad. Sci. USA* 83:9807–9811 Individual exons encode the integral membrane domains of human myelin proteolipid protein.
Duvall, et al. 1986 *Immunol Today* 7:115–119.
Endoh, M et al. 1986 *J Immunol* 137:3832–3835 DM–20, A Proteolipid Apoprotein, Is An Encephalitogen Of Acute And Relapsing Autoimmune Encephalomyelitis In Mice.
Greer, JM et al. 1992 *J Immunol* 149:783–788 Identification and Characterization of a Second Encephalitogenic Determinant of Myelin Proteolipid Protein (Residues 178–191) for SJL Mice.
Grima, B et al. 1992 *J Neurochem* 59:2318–2323 A Novel Transcript Overlapping the Myelin Basic Protein Gene.
Higgins, Paul J. et al. 1988 *J Immunol* 140:440–445. Suppression Of Experimental Autoimmune Encephalomyelitis by Oral Administration of Myelin Basic Protein and its Fragments.
Horvath, L et al. 1990 *Biochemistry* 29:2635–2638 Influence of Polar residue Deletions of Lipid–Protein Interactions with the Myelin Proteolipid Protein. Spin–Label ESR Studies with DM–20/Lipid Recombinants.
Johnson, D et al. 1986 *J Neuroimmunol* 13:99–108 Cell–Mediated Immunity to Myelin–Associated Glycoprotein, Proteolipid Protein, and Myelin Basci Protein in Multiple Sclerosis.
Kamholz, J et al. 1986 *Proc Natl Acad Sci USA* 83:4962–4966 Identification of three forms of human myelin basic protein by cDNA cloning.
Kamholz, J et al. 1988 *J Neurosci Res* 21:62–70 Organization and Expression of the Human Myelin Basic Protein Gene.
Kennedy, M et al. 1990 *J Immunol* 144:909–915 Inhibition of Murine Relapsing Experimental Autoimmune Encephalomyelitis by Immune Tolerance to Proteolipid Protein and its Encephalitogenic Peptides.
Kerlero De Rosbo, et al. 1993 *J Clin Invest* 92:2602–2608 Reactivity to Myelin Antigens in Multiple Sclerosis.
Kronquist, et al. 1987 *J Neurosci Res* 18:395–401 Expression of Myelin Proteins in the Developing Human Spinal Cord: Cloning and Sequencing of Human Proteolipid Protein cDNA.
Lehmann, PV et al. 1992 *Nature* 358:155–157 Spreading Of T–Cell Autoimmunity To Cryptic Determinants Of An Autoantigen.
Liblau, R et al. 1991 *Eur J Immunol* 21:1391–1395 T Cell Response To Myelin Basic Protein Epitopes In Multiple Sclerosis Patients And Healthy Subjects.
Martin, R et al. 1992 *Ann Rev Immunol* 10:153–187 Immunological Aspects of Demyelinating Diseases.
Martin, R et al. 1992 *J Immunol* 148:1359–1366 Diversity in Fine Specificity and T Cell Receptor Usage of the Human CD4+ Cytotoxic T Cell Response Specific for the Immunodominant Myelin Basic Protein Peptide 87–106.
Meinl, et al. 1993 *J Clin Invest* 92:2633–2643 Myelin Basic Protein–Specific T Lymphocyte Repertoire in Multiple Sclerosis.
Miller, A et al. 1992 *Neurology* 42(suppl 3):301 et seq. Active suppression Versus Clonal Anergy Following Oral or IV Administration of MBP in Actively and Passively Induced EAE.

Miller, A et al. 1992 *Proc. Natl. Acad. Sci. USA* 89:421–425 Suppressor T Cells generated by oral tolerization to myelin basic protein suppress both in vitro and in vivo immune responses by the release of transforming growth factor after antigen–specific triggering.

Miller, SD et al. 1994 *Immunol Today* 15:356–361 The Immunopathogenesis And Regulation Of T–Cell–Mediated Demyelinating Diseases.

Pette, M et al. 1990.*Neurology* 40:1770 Myelin Basic Protein–Specific T Lymphocyte Lines From MS Patients And Healthy Individuals.

Pham–Dinh, D et al. 1994 *J Neurochem* 63:2353–2356. Characterization and Expression of the cDNA Coding for the Human Myelin/Oligodendrocyte Glycoprotein.

Popot J, et al. 1991 *J. Memb. Biol.* 120:233–246 Major Myelin Proteolipid: The 4 Alpha–Helix Topology.

Proost P,et al. 1993 *Bioch. Biophys. Res. Com.* 192:1175–1181 Leukocyte Gelatinase B Cleavage Releases Encephalitogens from Human Myelin Basic Protein.

Qin, Y et al. 1989 *Eur J Immunol* 19:373–380 Resistance To Experimental Autoimmune Encephalomyelitis Induced By Neonatal Tolerization To Myelin Basic Protein: Clonal Elimination Vs. Regulation Of Autoaggressive Lymphocytes.

Racke MK et al. 1995 *J Immunol* 154:450–458 Retinoid Treatment of Experimental Allergic Encephalomyelitis—IL–4 Production Correlates with Improved Disease Course.

Richert JR et al. 1989. *J Neuroimmunol* 23:55–66 Evidence for multiple human T cell recognition sites on myelin basic protein.

Saeki, Y et al. 1992 *Proc Natl Acad Sci USA* 89:6157–6161 Transfer Of Multiple Sclerosis Into Severe Combined Immunodeficiency Mice By Mononuclear Cells From Cerebrospinal Fluid Of The Patients.

Sakai, et al. 1989 *Proc Natl Acad Sci* 86:9470–9474 Prevention of experimental encephalomyelitis with peptides that block interaction of T cells with major histocompatability complex proteins.

Salvetti, M et al. 1993 *Eur J Immunol* 23:1232–1239 Predominant And Stable T Cell Responses To Regions Of Myelin Basic Protein Can Be Detected In Individual Patients With Multiple Sclerosis.

Shpaer, E. 1986 *J Mol Biol* 188:555–564 Constraints on Codon Context in *Escherichia coli* Genes, Their Possible Role in Modulating the Efficiency of Translation.

Sobel RA et al. 1994 *Neurochem Res* 19:915–921 Minireview: Autoimmune Responses to Myelin Proteolipid Protein.

Su, X et al. 1991 *J Neuroimmunol* 34:181–190 Treatment Of Chronic Relapsing Experimental Allergic Encephalomyelitis With The Intravenous Administration Of Splenocytes Coupled To Encephalitogenic Peptide 91–103 Of Myelin Basic Protein.

Tuohy V, et al. 1994 *Neurochemical Research* 19:935–944 Peptide Determinants of Myelin Proteolipid Protein (PLP) in Autoimmune Demyelinating Disease: A Review*.

Utz, U et al. 1994 *Proc. Natl. Acad. Sci USA* 91:5567–5571 Heterogeneity Of T–Cell Receptor —Chain Complementarity–Determining Region 3 In Myelin Basic Protein–Specific T Cells Increases With Severity Of Multiple Sclerosis.

Van Der Veen, R et al. 1990 *J Neuroimmunol* 26:139–145 The Development And Characterization Of Encephalitogenic Cloned T Cells Specific For Myelin Proteolipid Protein.

Vandenbark, A et al. 1989 *Nature* 341:541–544 Immunization With A Synthetic T–Cell Receptor V–Region Peptide Protects Against Experimental Autoimmune Encephalomyelitis.

Voskuhl, RR et al. 1994 *J Immunol* 153:4834–4844 HLA Restriction And TCR Usage Of T Lymphocytes Specific For A Novel Candidate Autoantigen, X2 MBP, In Multiple Sclerosis.

Wada, K et al. 1992 *Nucl Acids Res* 20:(Supplement)2111–2118 Codon Usage Tabulated From The Genbank Genetic Sequence Data.

Wauben, MH et al. 1994 *J Immunol* 150:4211–4220 Inhibition Of Experimental Autoimmune Encephalomyelitis By MHC Class II Binding Competitor Peptides Depends On The Relative MHC Binding Affinity Of The Disease–Inducing Peptide.

Weimbs, T et al. 1992 *Biochemistry* 31:12289–12296 Proteolipid Protein (PLP) Of CNS Myelin: Positions Of Free, Disulfide–Bonded, And Fatty Acid Thioester–Linked Cysteine Residues And Implications For The Membrane Topology Of PLP.

Weiner, H et al. 1993 *Science* 259:1321–1324. Double–Blind Pilot Trial Of Oral Tolerization With Myelin Antigens In Multiple Sclerosis.

Whitham, R et al. 1991 *J Immunol* 147:3803–3808 Location Of A New Encephalitogenic Epitope (Residues 43 To 64) In Proteolipid Protein That Induces Relapsing Experimental Autoimmune Encephalomyelitis In PL/J And (SJL X PL)$F_1$ Mice.

Williams, DP et al. 1988 *Nucl Acids Res* 16:10453–10467 Design, Synthesis And Expression Of A Human Interleukin–2 Gene Incorporating The Codon Usage Bias Found In Highly Expressed *Escherichia coli* Genes.

Wucherpfenning, K et al. 1994 *J Immunol* 152:5581–5592 Clonal Expansion And Persistence Of Human T Cells Specific For An Immunodominant Myelin Basic Protein Peptide.

Yoon, 1993 *Science* 259:1263 MS Study Yields Mixed Results.

Zamvil, et al. 1986. *Nature* 324, 258–260 T cell epitope of the autoantigen myelin basic protein that induces encephalomyelitis.

Zhang J et al. 1992 *Ann Neurol* 32:330–338 Myelin Basic Protein–Specific T Lymphocytes in Multiple Sclerosis and Controls: Precursor Frequency, Fine specificity, and Cytotoxicity.

Zhang, J et al. 1993 *Science* 261:1451–1454 MHC–Restricted Depletion Of Human Myelin Basic Protein–Reactive T Cells By T Cell Vaccination.

Zhang, J et al. 1994 *J Exp Med* 179:973–984 Increased Frequency of Interleukin 2–responsive T Cells Specific for Myelin Basic Protein and Proteolipid Protein in Peripheral Blood and Cerebrospinal fluid of Patients with Multiple Sclerosis.

Pereyra, Pedro M., Elsa Horvath and Peter E. Braun. 1988, "Triton X–100 Extractions of Central Nervous System Myelin Indicate a Possible Role for the Minor Myelin Proteins in the Stability of Lamellae." *Neurochemical Research*, vol. 13, No. 6, pp. 583–595.

Roth, HJ et al. 1987 J Neurosci.Res 17:321–328:Evidence for the Expression of Four Myelin Basic Protein Variants in the Developing Human Spinal Cord Through cDNA Cloning.

Segal, et al. 1994 J. Neuroimmunol 51:7–19: Experimental Allergic encephalomyelitis Induced by the Peptide Encoded by Exon 2 of the MBP Gene, A Peptide Implicated in Remyelination.

Sercarz et al. 1959 Nature vol. 184: 1080–1082–Specific Inhibition of Antibody Formation During Immunological Paralysis and Unresponsiveness.

Smith et al. Nature vol. 337 Jan. 12, 1989–Antibodies to CD3/T–cell receptor Complex Induce Death By Apoptosis in Immature T Cells in Thymic Cultures. pp. 181–184.

Sriram et al. Cellular Immunology 75, 378–382 (1983)–Administration of Myelin Basic Protein–Coupled Spleen Cells Prevents Experimental Allergic Encephalitis.

Streicher and Stoffel: 1989. Biol. Chem Hoppe–Seyler 370:503–510: The Organization of The Human Myelin Basic Protein Gene, Comparasion with the Mouse Gene.

Traugott, U. et al. 1982. J Neurol Sci 56:65–73: Chronic Relapsing Experimental Autoimmune Encephalomyelitis, treatment with Combination of Myelin Components Promotes Clinical and Structural Recovery.

Tuohy, V. et al. 1992 J. Neuroimmunol: 39: 67–74: Myelin Proteolipid Protein: Minimum Sequence Requirements for Active Induction of Autoimmune Encephalomyelitis in SWR/J and SJL/Mice.

Van Der Veen, R. et al. 1992 J. Neuroimmunol 38: 139–146: Immune Processing of Proteolipid Protein By Subsets of Antigen–Presenting Spleen Cells.

Van Noort, J. et al. 1994 J Chromatogr B. 653:155–161: Fractionaltion of Central Nervous System Myelin Proteins by Reversed–Phase High–Performance Liquid Chromatography.

Voskull, R. et al. 1993 J. Neuroimmunol: 42: 187–192 T–Lymphocyte Recognition of a Portion of Myelin Basic Protien Encoded by an Exon Expressed During Myelination.

Voskuhl R. et al. 1993 J. Neuroimmunol 46: 137–144: A Novel Candidate Autoantigen in a Multiplex Family with Multiple Sclerosis: Prevalence of T–Lympocytes Specific For and MBP Epitope Unique to Myelination.

Whitham, R. et al 1991: J. Immunol 14 101–107: Lymphocytes From SJL/J Mice Immunized with Spinal Cord Respond Selectively to a Peptide of Proteolipid Protein and Transfer Relapsing Demyelinating Experimental Autoimmune Encephalomyelitis.

Wen et al. J. clin. Invest vol. 102, No. 5, Sep. 1998, 947–957–Induction of Insulitis by Glutamic Acid Decarboxylase Peptide–Specific and HLA–DQ8–restricted CD4 T Cells from Human DQ Transgenic Mice.

Fritz, RB et al. 1994 J. Neuroimmunol 51:1–6: Encephalitognicity of Myelin basic Protein Exon–2 Peptide in Mice.

Griffin et al., 1995 Am J. Pathel 147:845–857.

Herman, RA et al. 1992 Biochemistry 31:8619–8628: Human Hemoglobin Expression in *Escherichia Coli*: Importance of Optimal Codon Usage.

Kaufman et al., 1992 J Clin Invest 98:283–292.

Kim et al., 1993:Immunol Invest 22 (3):219–227.

Lockshin and Zekeri, 1991: Apoptosis: The Molecular Basis of Cell Death, Tomei and Cope (eds), cold Spring Harbor Laboratory Press, Planview, New York, pp. 47–60.

Lohmann et al., 1994 Lancet 343:1607–1608.

McRae, B. et al. 1992 J Neuroimmunol 38:229–240: Induction of Active and Adoptive Relapsing Experimental Autoimmune Encephalomyelitis (EAE) Using an Encephalitogenic Epitope of Proteolipid Protein.

Miller, A. et al. 1992 J Neuroimmunol 39:243–350.

Mitchinson 1964 Proc R. Soc London Ser B 161:275–280: Induction of Immunological Paralysis in teo zones of dosage.

Mullis et al., Eds., 1994 The Polymerase Chain Reaction Springer–Verlag, New York, NY. pp. 263–273.

Oettinger. H. et al. 1993 J Neuroimmunol 44:157–162. Biological Activity of Recombinant Human Myelin Basic Protein.

Pelfrey et al., 1993 J Neuroimmunol 46:33–42: Identification of Novel T Cell Eptiope of Human Proteolipid (residues 40–60) Recognized by Proliferative and Cytolytic CD4+T cells From Multiple Sclereosis Patients.

Pelfrey et al. 1994 J Neuroimmunol 53:153–161: Identification of A Second T Cell Epitope of Human Proteolipid Protein (residues 89–106) recognized by proliferative and Cytolytic CD4+t Cells from Multiple Sclereosis Patients.

Barnett, LA et al. 1993 J Neuroimmunol 44:15–26;Enhancement of Autoimmune Disease Using Recombinant Vaccinia Virus Encoding Myelin Proteolipid Protein.

Chiang, B–L et al. 1992 Int. Arch Allergy Immonol 98:181–188: Prospects of Vaccination in Autoimmune Disease.

Chou, YK et al 1992. J. Neuroimmunol 38: 105–114: Frequency of T Cells Specific for Myelin Basic Protien and Myelin Proteolipid Protien in Blood and Cerebrospinal Fluid in Multiple Sclerosis.

Einstein et al. 1962: J. Neurochem: 9:252–361: The isolation from bovine spinal cord of a homogeneous protein with Encephalitgenic Activities.

* cited by examiner

IG1

IG2

IG3

☐ Insulin B
■ Insulin C
▦ hGAD65/115-127
▩ hGAD65/247-286
▨ hGAD65/473-5--

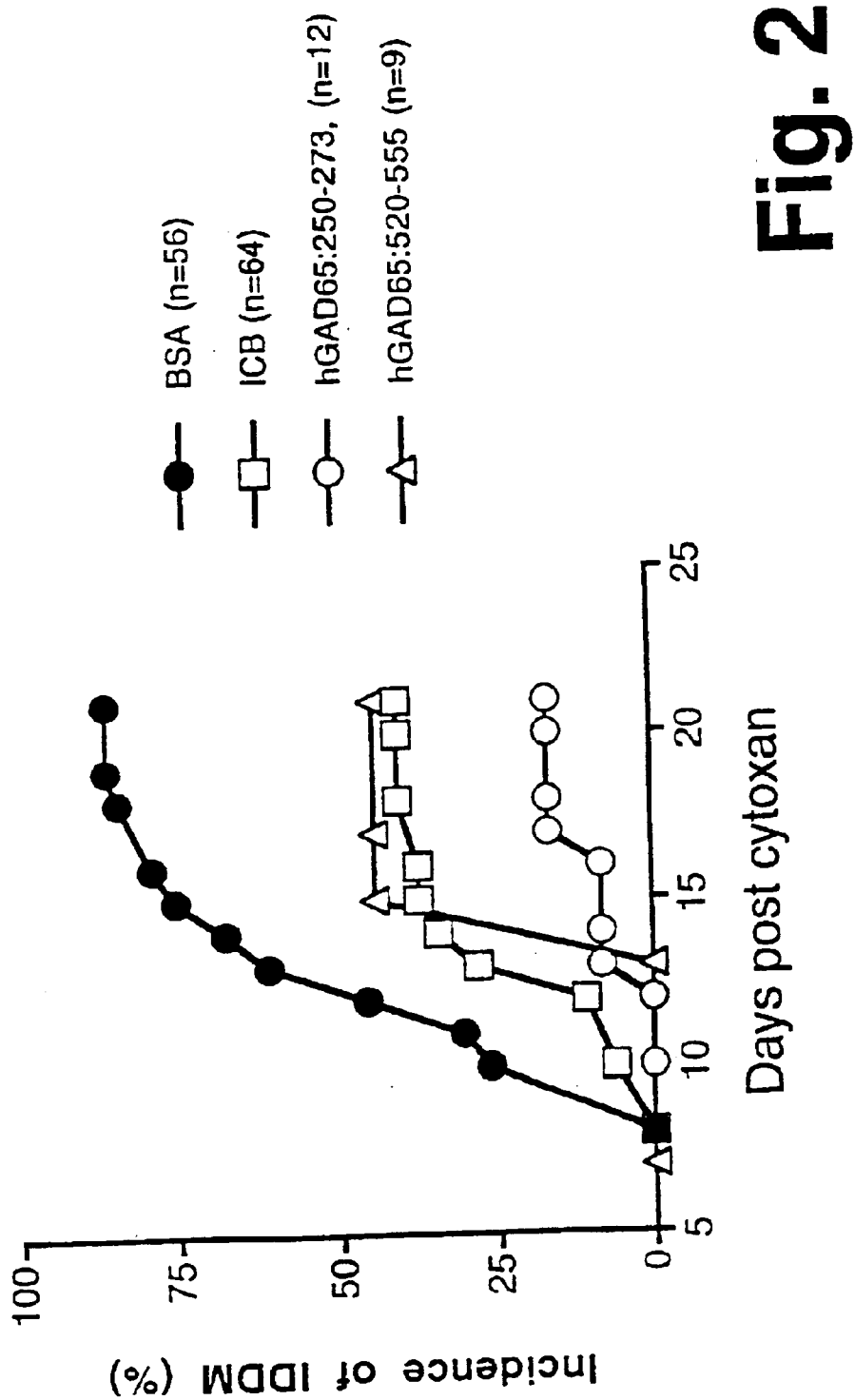

IG5 H6

☐ Insulin B chain (aa 1-31)
■ Insulin C Peptide (aa 32-67)
▦ hGAD65/202-236-GGG (aa 68-105)
▦ hGAD65/115-127 (aa 106-118)
☐ hGAD65/247-300 (aa 119-175, GGG at aa 146-148)
▨ GGG-hGAD65/508-555 (aa 176-227)

SEQUENCE LISTING

<160> NUMBER OF SEQ ID NOS: 37

<210> SEQ ID NO 1
<211> LENGTH: 160
<212> TYPE: PRT
<213> ORGANISM: Artificial Sequence
<220> FEATURE:
<223> OTHER INFORMATION: IG1 Infusion Protein

<400> SEQUENCE: 1

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Asn Met Tyr Ala Met Met Ile Ala Arg Phe
        35                  40                  45

Lys Met Phe Pro Glu Val Lys Glu Lys Gly Met Ala Ala Leu Pro Arg
    50                  55                  60

Leu Ile Ala Phe Thr Ser Glu Lys Cys Leu Glu Leu Ala Glu Tyr Leu
65                  70                  75                  80

Tyr Asn Ile Ile Lys Asn Arg Glu Gly Tyr Glu Met Val Phe Asp Gly
                85                  90                  95

Lys Pro Gln His Thr Asn Val Cys Phe Trp Tyr Ile Pro Pro Ser Leu
            100                 105                 110

Arg Thr Leu Glu Asp Asn Glu Glu Arg Met Ser Arg Leu Ser Lys Val
        115                 120                 125

Ala Pro Val Ile Lys Ala Arg Met Met Glu Tyr Gly Thr Thr Met Val
    130                 135                 140

Ser Tyr Gln Pro Leu Gly Asp Lys Val Asn His His His His His His
145                 150                 155                 160

<210> SEQ ID NO 2
<211> LENGTH: 180
<212> TYPE: PRT
<213> ORGANISM: Artificial Sequence
<220> FEATURE:
<223> OTHER INFORMATION: IG2 Fusion Protein

<400> SEQUENCE: 2

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Met Asn Ile Leu Leu Gln Tyr Val Val Lys
        35                  40                  45

Ser Phe Asp Asn Met Tyr Ala Met Met Ile Ala Arg Phe Lys Met Phe
    50                  55                  60

Pro Glu Val Lys Glu Lys Gly Met Ala Ala Leu Pro Arg Leu Ile Ala
65                  70                  75                  80

Phe Thr Ser Glu His Ser His Phe Ser Leu Lys Lys Cys Leu Glu Leu
                85                  90                  95

Ala Glu Tyr Leu Tyr Asn Ile Ile Lys Asn Arg Glu Gly Tyr Glu Met
            100                 105                 110

Val Phe Asp Gly Lys Pro Gln His Thr Asn Val Cys Phe Trp Tyr Ile
        115                 120                 125

Pro Pro Ser Leu Arg Thr Leu Glu Asp Asn Glu Glu Arg Met Ser Arg

-continued

```
              130                 135                 140
Leu Ser Lys Val Ala Pro Val Ile Lys Ala Arg Met Met Glu Tyr Gly
145                 150                 155                 160

Thr Thr Met Val Ser Tyr Gln Pro Leu Gly Asp Lys Val Asn His His
                165                 170                 175

His His His His
            180

<210> SEQ ID NO 3
<211> LENGTH: 144
<212> TYPE: PRT
<213> ORGANISM: Artificial Sequence
<220> FEATURE:
<223> OTHER INFORMATION: IG3 Fusion Protein

<400> SEQUENCE: 3

Met Phe Val Asn Gln His Leu Cys Gly Ser His Leu Val Glu Ala Leu
1               5                   10                  15

Trp Leu Val Cys Gly Glu Arg Gly Phe Phe Tyr Thr Pro Lys Thr Arg
                20                  25                  30

Arg Glu Ala Glu Asp Leu Met Asn Ile Leu Leu Gln Tyr Val Val Lys
            35                  40                  45

Ser Phe Asp Asn Met Tyr Ala Met Met Ile Ala Arg Phe Lys Met Phe
50                  55                  60

Pro Glu Val Lys Glu Lys Gly Met Ala Ala Leu Pro Arg Leu Ile Ala
65                  70                  75                  80

Phe Thr Ser Glu His Ser His Phe Ser Leu Lys Lys Cys Leu Glu Leu
                85                  90                  95

Ala Glu Tyr Leu Tyr Asn Ile Ile Lys Asn Arg Glu Gly Tyr Glu Met
            100                 105                 110

Val Phe Asp Gly Lys Pro Gln His Thr Asn Val Cys Phe Trp Tyr Ile
        115                 120                 125

Pro Pro Ser Leu Arg Thr Leu Glu Asp Asn His His His His His
    130                 135                 140

<210> SEQ ID NO 4
<211> LENGTH: 181
<212> TYPE: PRT
<213> ORGANISM: Artificial Sequence
<220> FEATURE:
<223> OTHER INFORMATION: IG4 Fusion Protein

<400> SEQUENCE: 4

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
                20                  25                  30

Arg Glu Ala Glu Asp Leu Gln Val Gly Gln Val Glu Leu Gly Gly Gly
            35                  40                  45

Pro Gly Ala Gly Ser Leu Gln Pro Leu Ala Leu Glu Gly Ser Leu Gln
50                  55                  60

Lys Arg Gly Thr Asn Met Phe Thr Tyr Glu Ile Ala Pro Val Phe Val
65                  70                  75                  80

Leu Leu Glu Tyr Val Thr Leu Lys Lys Met Arg Glu Ile Ile Gly Trp
                85                  90                  95

Pro Gly Gly Ser Gly Asp Gly Gly Met Asn Ile Leu Leu Gln Tyr
            100                 105                 110
```

```
Val Val Lys Ser Phe Asp Asn Met Tyr Ala Met Met Ile Ala Arg Phe
            115                 120                 125

Lys Met Phe Pro Glu Val Lys Glu Lys Gly Met Ala Ala Leu Pro Arg
        130                 135                 140

Leu Gly Gly Gly Ile Ala Phe Thr Ser Glu His Ser His Phe Ser Leu
145                 150                 155                 160

Lys Lys Gly Ala Ala Ala Leu Gly Ile Gly Thr Asp Ser Val Ile His
                165                 170                 175

His His His His His
            180

<210> SEQ ID NO 5
<211> LENGTH: 232
<212> TYPE: PRT
<213> ORGANISM: Artificial Sequence
<220> FEATURE:
<223> OTHER INFORMATION: IG5 Fusion Protein

<400> SEQUENCE: 5

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Gln Val Gly Gln Val Glu Leu Gly Gly Gly
        35                  40                  45

Pro Gly Ala Gly Ser Leu Gln Pro Leu Ala Leu Glu Gly Ser Leu Gln
50                  55                  60

Lys Arg Gly Thr Asn Met Phe Thr Tyr Glu Ile Ala Pro Val Phe Val
65                  70                  75                  80

Leu Leu Glu Tyr Val Thr Leu Lys Lys Met Arg Glu Ile Ile Gly Trp
                85                  90                  95

Pro Gly Gly Ser Gly Asp Gly Gly Met Asn Ile Leu Leu Gln Tyr
            100                 105                 110

Val Val Lys Ser Phe Asp Asn Met Tyr Ala Met Met Ile Ala Arg Phe
            115                 120                 125

Lys Met Phe Pro Glu Val Lys Glu Lys Gly Met Ala Ala Leu Pro Arg
        130                 135                 140

Leu Gly Gly Gly Ile Ala Phe Thr Ser Glu His Ser His Phe Ser Leu
145                 150                 155                 160

Lys Lys Gly Ala Ala Ala Leu Gly Ile Gly Thr Asp Ser Val Ile Gly
                165                 170                 175

Gly Gly Tyr Ile Pro Pro Ser Leu Arg Thr Leu Glu Asp Asn Glu Glu
            180                 185                 190

Arg Met Ser Arg Leu Ser Lys Val Ala Pro Val Ile Lys Ala Arg Met
        195                 200                 205

Met Glu Tyr Gly Thr Thr Met Val Ser Tyr Gln Pro Leu Gly Asp Lys
    210                 215                 220

Val Asn His His His His His His
225                 230

<210> SEQ ID NO 6
<211> LENGTH: 393
<212> TYPE: PRT
<213> ORGANISM: Artificial Sequence
<220> FEATURE:
<223> OTHER INFORMATION: IG6 Fusion Protein

<400> SEQUENCE: 6
```

```
Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
                20                  25                  30

Arg Glu Ala Glu Asp Leu Gln Val Gly Gln Val Glu Leu Gly Gly Gly
                35                  40                  45

Pro Gly Ala Gly Ser Leu Gln Pro Leu Ala Leu Glu Gly Ser Leu Gln
    50                  55                  60

Lys Arg Gly Thr Asn Met Phe Thr Tyr Glu Ile Ala Pro Val Phe Val
65                  70                  75                  80

Leu Leu Glu Tyr Val Thr Leu Lys Lys Met Arg Glu Ile Ile Gly Trp
                85                  90                  95

Pro Gly Gly Ser Gly Asp Gly Gly Gly Met Asn Ile Leu Leu Gln Tyr
                100                 105                 110

Val Val Lys Ser Phe Asp Asn Met Tyr Ala Met Met Ile Ala Arg Phe
            115                 120                 125

Lys Met Phe Pro Glu Val Lys Glu Lys Gly Met Ala Ala Leu Pro Arg
            130                 135                 140

Leu Gly Gly Gly Ile Ala Phe Thr Ser Glu His Ser His Phe Ser Leu
145                 150                 155                 160

Lys Lys Gly Ala Ala Ala Leu Gly Ile Gly Thr Asp Ser Val Ile Gly
                165                 170                 175

Gly Gly Ile Glu His Asp Pro Arg Met Pro Ala Tyr Ile Ala Thr Gln
                180                 185                 190

Gly Pro Leu Ser His Thr Ile Ala Asp Phe Trp Gln Met Val Trp Glu
    195                 200                 205

Ser Gly Cys Thr Val Ile Val Met Leu Thr Pro Leu Val Glu Asp Gly
    210                 215                 220

Val Lys Gln Cys Asp Arg Tyr Trp Pro Asp Glu Gly Ala Ser Leu Tyr
225                 230                 235                 240

His Val Tyr Glu Val Asn Leu Val Ser Glu His Ile Trp Cys Glu Asp
                245                 250                 255

Phe Leu Val Arg Ser Phe Tyr Leu Lys Asn Val Gln Thr Gln Glu Thr
            260                 265                 270

Arg Thr Leu Thr Gln Phe His Phe Leu Ser Trp Pro Ala Glu Gly Thr
            275                 280                 285

Pro Ala Ser Thr Arg Pro Leu Leu Asp Phe Arg Arg Lys Val Asn Lys
            290                 295                 300

Cys Tyr Arg Gly Arg Ser Cys Pro Ile Ile Val His Cys Ser Asp Gly
305                 310                 315                 320

Ala Gly Arg Thr Gly Thr Tyr Ile Leu Ile Asp Met Val Leu Asn Arg
                325                 330                 335

Met Ala Lys Gly Val Lys Glu Ile Asp Ile Ala Ala Thr Leu Glu His
                340                 345                 350

Val Arg Asp Gln Arg Pro Gly Leu Val Arg Ser Lys Asp Gln Phe Glu
            355                 360                 365

Phe Ala Leu Thr Ala Val Ala Glu Glu Val Asn Ala Ile Leu Lys Ala
            370                 375                 380

Leu Pro Gln His His His His His His
385                 390
```

<210> SEQ ID NO 7
<211> LENGTH: 444

-continued

<212> TYPE: PRT
<213> ORGANISM: Artificial Sequence
<220> FEATURE:
<223> OTHER INFORMATION: IG7 Fusion Protein

<400> SEQUENCE: 7

```
Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Gln Val Gly Gln Val Glu Leu Gly Gly Gly
        35                  40                  45

Pro Gly Ala Gly Ser Leu Gln Pro Leu Ala Leu Glu Gly Ser Leu Gln
50                  55                  60

Lys Arg Gly Thr Asn Met Phe Thr Tyr Glu Ile Ala Pro Val Phe Val
65                  70                  75                  80

Leu Leu Glu Tyr Val Thr Leu Lys Lys Met Arg Glu Ile Ile Gly Trp
                85                  90                  95

Pro Gly Gly Ser Gly Asp Gly Gly Met Asn Ile Leu Leu Gln Tyr
            100                 105                 110

Val Val Lys Ser Phe Asp Asn Met Tyr Ala Met Met Ile Ala Arg Phe
            115                 120                 125

Lys Met Phe Pro Glu Val Lys Glu Lys Gly Met Ala Ala Leu Pro Arg
        130                 135                 140

Leu Gly Gly Ile Ala Phe Thr Ser Glu His Ser His Phe Ser Leu
145                 150                 155                 160

Lys Lys Gly Ala Ala Ala Leu Gly Ile Gly Thr Asp Ser Val Ile Gly
                165                 170                 175

Gly Gly Tyr Ile Pro Pro Ser Leu Arg Thr Leu Glu Asp Asn Glu Glu
            180                 185                 190

Arg Met Ser Arg Leu Ser Lys Val Ala Pro Val Ile Lys Ala Arg Met
        195                 200                 205

Met Glu Tyr Gly Thr Thr Met Val Ser Tyr Gln Pro Leu Gly Asp Lys
210                 215                 220

Val Asn Gly Gly Gly Ile Glu His Asp Pro Arg Met Pro Ala Tyr Ile
225                 230                 235                 240

Ala Thr Gln Gly Pro Leu Ser His Thr Ile Ala Asp Phe Trp Gln Met
                245                 250                 255

Val Trp Glu Ser Gly Cys Thr Val Ile Val Met Leu Thr Pro Leu Val
            260                 265                 270

Glu Asp Gly Val Lys Gln Cys Asp Arg Tyr Trp Pro Asp Glu Gly Ala
        275                 280                 285

Ser Leu Tyr His Val Tyr Glu Val Asn Leu Val Ser Glu His Ile Trp
290                 295                 300

Cys Glu Asp Phe Leu Val Arg Ser Phe Tyr Leu Lys Asn Val Gln Thr
305                 310                 315                 320

Gln Glu Thr Arg Thr Leu Thr Gln Phe His Phe Leu Ser Trp Pro Ala
                325                 330                 335

Glu Gly Thr Pro Ala Ser Thr Arg Pro Leu Leu Asp Phe Arg Arg Lys
            340                 345                 350

Val Asn Lys Cys Tyr Arg Gly Arg Ser Cys Pro Ile Ile Val His Cys
        355                 360                 365

Ser Asp Gly Ala Gly Arg Thr Gly Thr Tyr Ile Leu Ile Asp Met Val
370                 375                 380
```

```
Leu Asn Arg Met Ala Lys Gly Val Lys Glu Ile Asp Ile Ala Ala Thr
385                 390                 395                 400

Leu Glu His Val Arg Asp Gln Arg Pro Gly Leu Val Arg Ser Lys Asp
                405                 410                 415

Gln Phe Glu Phe Ala Leu Thr Ala Val Ala Glu Glu Val Asn Ala Ile
            420                 425                 430

Leu Lys Ala Leu Pro Gln His His His His His His
        435                 440
```

<210> SEQ ID NO 8
<211> LENGTH: 173
<212> TYPE: PRT
<213> ORGANISM: Artificial Sequence
<220> FEATURE:
<223> OTHER INFORMATION: IG4NHB hypothetical fusion protein

<400> SEQUENCE: 8

```
Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Gln Val Gly Gln Val Glu Leu Gly Gly Gly
        35                  40                  45

Pro Gly Ala Gly Ser Leu Gln Pro Leu Ala Leu Glu Gly Ser Leu Gln
    50                  55                  60

Lys Arg Gly Met Asn Ile Leu Leu Gln Tyr Val Val Lys Ser Phe Asp
65                  70                  75                  80

Asn Met Tyr Ala Met Met Ile Ala Arg Phe Lys Met Phe Pro Glu Val
                85                  90                  95

Lys Glu Lys Gly Met Ala Ala Leu Pro Arg Leu Ile Ala Phe Thr Ser
            100                 105                 110

Glu His Ser His Phe Ser Leu Lys Lys Cys Leu Glu Leu Ala Glu Tyr
        115                 120                 125

Leu Tyr Asn Ile Ile Lys Asn Arg Glu Gly Tyr Glu Met Val Phe Asp
    130                 135                 140

Gly Lys Pro Gln His Thr Asn Val Cys Phe Trp Tyr Ile Pro Pro Ser
145                 150                 155                 160

Leu Arg Thr Leu Glu Asp Asn His His His His His
                165                 170
```

<210> SEQ ID NO 9
<211> LENGTH: 3
<212> TYPE: PRT
<213> ORGANISM: Artificial Sequence
<220> FEATURE:
<223> OTHER INFORMATION: Helix breaker

<400> SEQUENCE: 9

```
Pro Pro Pro
    1
```

<210> SEQ ID NO 10
<211> LENGTH: 3
<212> TYPE: PRT
<213> ORGANISM: Artificial Sequence
<220> FEATURE:
<223> OTHER INFORMATION: Helix breaker

<400> SEQUENCE: 10

```
Gly Gly Gly
    1
```

```
<210> SEQ ID NO 11
<211> LENGTH: 139
<212> TYPE: DNA
<213> ORGANISM: Artificial Sequence
<220> FEATURE:
<223> OTHER INFORMATION: prIG1 primer

<400> SEQUENCE: 11
catatgttcg ttaaccagca tctgtgtggc tctcacctgg ttgaagccct gtatctggtt        60
tgcggtgaac gcggcttttt ctacaccccg aaaacccgtc gtgaagcgga agatctgaac       120
atgtatgcca tgatgatcg                                                   139

<210> SEQ ID NO 12
<211> LENGTH: 143
<212> TYPE: DNA
<213> ORGANISM: Artificial Sequence
<220> FEATURE:
<223> OTHER INFORMATION: prIG2 primer

<400> SEQUENCE: 12
ggtttttaat gatgttgtac agatattccg ccagttccag acatttttca gaggtaaagg        60
caatcagacg cggcagcgcg gccataccct tttctttaac ttccgggaac attttaaagc       120
gcgcgatcat catggcatac atg                                              143

<210> SEQ ID NO 13
<211> LENGTH: 138
<212> TYPE: DNA
<213> ORGANISM: Artificial Sequence
<220> FEATURE:
<223> OTHER INFORMATION: prIG3 prmer

<400> SEQUENCE: 13
gtacaacatc attaaaaacc gcgaaggcta tgaaatggtt ttcgatggta aaccgcagca        60
taccaacgtt tgcttttggt acatcccgcc gagcctgcgt accctggaag ataacgaaga       120
acgcatgagc cgtctgtc                                                    138

<210> SEQ ID NO 14
<211> LENGTH: 132
<212> TYPE: DNA
<213> ORGANISM: Artificial Sequence
<220> FEATURE:
<223> OTHER INFORMATION: prIG4 primer

<400> SEQUENCE: 14
ggatccttaa tggtgatggt gatggtggtt aactttatca cccagcggct ggtagctaac        60
catggtggtg ccatattcca tcatgcgcgc tttaataacc ggggcaactt tagacagacg       120
gctcatgcgt tc                                                          132

<210> SEQ ID NO 15
<211> LENGTH: 18
<212> TYPE: DNA
<213> ORGANISM: Artificial Sequence
<220> FEATURE:
<223> OTHER INFORMATION: prIG5 primer

<400> SEQUENCE: 15
catatgttcg ttaaccag                                                     18
```

```
<210> SEQ ID NO 16
<211> LENGTH: 18
<212> TYPE: DNA
<213> ORGANISM: Artificial Sequence
<220> FEATURE:
<223> OTHER INFORMATION: prIG6 primer

<400> SEQUENCE: 16
ggatccttaa tggtgatg                                                   18

<210> SEQ ID NO 17
<211> LENGTH: 492
<212> TYPE: DNA
<213> ORGANISM: Artificial Sequence
<220> FEATURE:
<223> OTHER INFORMATION: IG1 Fusion Protein coding sequence

<400> SEQUENCE: 17
catatgttcg ttaaccagca tctgtgtggc tctcacctgg ttgaagccct gtatctggtt     60
tgcggtgaac gcggctttttt ctacaccccg aaaacccgtc gtgaagcgga agatctgaac    120
atgtatgcca tgatgatcgc gcgctttaaa atgttcccgg aagttaaaga aaaaggtatg    180
gccgcgctgc gcgtctgat tgcctttacc tctgaaaaat gtctggaact ggcggaatat     240
ctgtacaaca tcattaaaaa ccgcgaaggc tatgaaatgg ttttcgatgg taaaccgcag    300
cataccaacg tttgcttttg gtacatcccg ccgagcctgc gtaccctgga agataacgaa    360
gaacgcatga gccgtctgtc taaagttgcc ccggttatta agcgcgcat gatggaatat     420 ggcaccacca tggttagcta ccagccgctg ggtgataaag ttaaccacca tcaccatcac    480
cattaaggat cc                                                         492

<210> SEQ ID NO 18
<211> LENGTH: 64
<212> TYPE: DNA
<213> ORGANISM: Artificial Sequence
<220> FEATURE:
<223> OTHER INFORMATION: prIG7 primer

<400> SEQUENCE: 18
agatctgatg aacattctgc tgcagtatgt tgttaaaagc ttcgataaca tgtatgccat     60
gatg                                                                  64

<210> SEQ ID NO 19
<211> LENGTH: 78
<212> TYPE: DNA
<213> ORGANISM: Artificial Sequence
<220> FEATURE:
<223> OTHER INFORMATION: prIG8 primer

<400> SEQUENCE: 19
tgtacagata ttccgccagt tccagacatt ttttcagaga aaaatggcta tgttcagagg     60
taaaggcaat cagacgcg                                                   78

<210> SEQ ID NO 20
<211> LENGTH: 27
<212> TYPE: DNA
<213> ORGANISM: Artificial Sequence
<220> FEATURE:
<223> OTHER INFORMATION: prIG12 primer

<400> SEQUENCE: 20
tgtacagata ttccgccagt tccagac                                         27
```

<210> SEQ ID NO 21
<211> LENGTH: 552
<212> TYPE: DNA
<213> ORGANISM: Artificial Sequence
<220> FEATURE:
<223> OTHER INFORMATION: IG2 Fusion Protein coding sequence

<400> SEQUENCE: 21

```
catatgttcg ttaaccagca tctgtgtggc tctcacctgg ttgaagccct gtatctggtt      60
tgcggtgaac gcggctttt ctacaccccg aaaacccgtc gtgaagcgga agatctgatg     120
aacattctgc tgcagtatgt tgttaaaagc ttcgataaca tgtatgccat gatgatcgcg     180
cgctttaaaa tgttcccgga agttaaagaa aaaggtatgg ccgcgctgcc gcgtctgatt     240
gcctttacct ctgaacatag ccattttttct ctgaaaaaat gtctggaact ggcggaatat     300
ctgtacaaca tcattaaaaa ccgcgaaggc tatgaaatgg ttttcgatgg taaaccgcag     360
cataccaacg tttgcttttg gtacatcccg ccgagcctgc gtaccctgga agataacgaa     420
gaacgcatga gccgtctgtc taaagttgcc ccggttatta agcgcgcat gatggaatat     480
ggcaccacca tggttagcta ccagccgctg ggtgataaag ttaaccacca tcaccatcac     540
cattaaggat cc                                                         552
```

<210> SEQ ID NO 22
<211> LENGTH: 46
<212> TYPE: DNA
<213> ORGANISM: Artificial Sequence
<220> FEATURE:
<223> OTHER INFORMATION: prIG13 primer

<400> SEQUENCE: 22

```
ggatccttaa atggtgatgg tgatggtggt tatcttccag ggtacg                     46
```

<210> SEQ ID NO 23
<211> LENGTH: 444
<212> TYPE: DNA
<213> ORGANISM: Artificial Sequence
<220> FEATURE:
<223> OTHER INFORMATION: IG3 Fusion Protein coding sequence

<400> SEQUENCE: 23

```
catatgttcg ttaaccagca tctgtgtggc tctcacctgg ttgaagccct gtatctggtt      60
tgcggtgaac gcggctttt ctacaccccg aaaacccgtc gtgaagcgga agatctgatg     120
aacattctgc tgcagtatgt tgttaaaagc ttcgataaca tgtatgccat gatgatcgcg     180
cgctttaaaa tgttcccgga agttaaagaa aaaggtatgg ccgcgctgcc gcgtctgatt     240
gcctttacct ctgaacatag ccattttttct ctgaaaaaat gtctggaact ggcggaatat     300
ctgtacaaca tcattaaaaa ccgcgaaggc tatgaaatgg ttttcgatgg taaaccgcag     360
cataccaacg tttgcttttg gtacatcccg ccgagcctgc gtaccctgga agataaccac     420
catcaccatc accattaagg atcc                                            444
```

<210> SEQ ID NO 24
<211> LENGTH: 555
<212> TYPE: DNA
<213> ORGANISM: Artificial Sequence
<220> FEATURE:
<223> OTHER INFORMATION: IG4 Fusion Protein coding sequence

<400> SEQUENCE: 24

```
catatgttcg ttaaccagca tctgtgtggc tctcacctgg ttgaagccct gtatctggtt      60
```

-continued

```
tgcggtgaac gcggctttt ctacaccccg aaacccgtc gtgaagcgga agatctgcag      120
gtggggcagg tggagctggg cggggccct ggtgcaggca gcctgcagcc cttggccctg      180
gaggggtccc tgcagaagcg tggcactaac atgttcacct atgaaattgc tccagtattt      240
gtgcttttgg aatatgtcac actaaagaaa atgagagaaa tcattggctg ccagggggc      300 tctggcgatg gaggcggtat gaacattctg ctgcagtatg ttgttaaaag cttcgataac      360
atgtatgcca tgatgatcgc gcgctttaaa atgttcccgg aagttaaaga aaaggtatg      420 gccgcgctgc cgcgtctggg aggcggtatt gcctttacct ctgaacatag ccattttct      480 ctgaaaaaag gagctgcagc cttagggatt ggaacagaca gcgtgattca ccatcaccat      540
caccattaag gatcc                                                       555
```

```
<210> SEQ ID NO 25
<211> LENGTH: 24
<212> TYPE: DNA
<213> ORGANISM: Artificial Sequence
<220> FEATURE:
<223> OTHER INFORMATION: prIG14 primer

<400> SEQUENCE: 25
catatgttcg ttaaccagca tctg                                              24
```

```
<210> SEQ ID NO 26
<211> LENGTH: 69
<212> TYPE: DNA
<213> ORGANISM: Artificial Sequence
<220> FEATURE:
<223> OTHER INFORMATION: prIG15 primer

<400> SEQUENCE: 26
gctgcctgca ccagggcccc cgcccagctc cacctgcccc acctgcagat cttccgcttc      60
acgacgggt                                                              69
```

```
<210> SEQ ID NO 27
<211> LENGTH: 66
<212> TYPE: DNA
<213> ORGANISM: Artificial Sequence
<220> FEATURE:
<223> OTHER INFORMATION: prIG16 primer

<400> SEQUENCE: 27
agtgccacgc ttctgcaggg acccctccag ggccaagggc tgcaggctgc ctgcaccagg      60
gccccc                                                                 66
```

```
<210> SEQ ID NO 28
<211> LENGTH: 69
<212> TYPE: DNA
<213> ORGANISM: Artificial Sequence
<220> FEATURE:
<223> OTHER INFORMATION: prIG17 primer

<400> SEQUENCE: 28
ttccaaaagc acaaatactg gagcaatttc ataggtgaac atgttagtgc cacgcttctg      60
cagggaccc                                                              69
```

```
<210> SEQ ID NO 29
<211> LENGTH: 69
<212> TYPE: DNA
<213> ORGANISM: Artificial Sequence
<220> FEATURE:
```

```
<223> OTHER INFORMATION: prIG18 primer

<400> SEQUENCE: 29
ccctggccag ccaatgattt ctctcatttt ctttagtgtg acatattcca aaagcacaaa      60
tactggagc                                                              69

<210> SEQ ID NO 30
<211> LENGTH: 69
<212> TYPE: DNA
<213> ORGANISM: Artificial Sequence
<220> FEATURE:
<223> OTHER INFORMATION: prIG19 primer

<400> SEQUENCE: 30
agagaaatca ttggctggcc aggggctct ggcgatggag gcggtatgaa cattctgctg       60
cagtatgtt                                                              69

<210> SEQ ID NO 31
<211> LENGTH: 68
<212> TYPE: DNA
<213> ORGANISM: Artificial Sequence
<220> FEATURE:
<223> OTHER INFORMATION: prIG20 primer

<400> SEQUENCE: 31
cagagaaaaa tggctatgtt cagaggtaaa ggcaataccg cctcccagac gcggcagcgc      60
ggccatac                                                               68

<210> SEQ ID NO 32
<211> LENGTH: 69
<212> TYPE: DNA
<213> ORGANISM: Artificial Sequence
<220> FEATURE:
<223> OTHER INFORMATION: prIG21 primer

<400> SEQUENCE: 32
aatcacgctg tctgttccaa tccctaaggc tgcagctcct tttttcagag aaaaatggct      60
atgttcaga                                                              69

<210> SEQ ID NO 33
<211> LENGTH: 60
<212> TYPE: DNA
<213> ORGANISM: Artificial Sequence
<220> FEATURE:
<223> OTHER INFORMATION: prIG22 primer

<400> SEQUENCE: 33
ttagggattg aacagacag cgtgattgga ggcggttaca tcccgccgag cctgcgtacc       60

<210> SEQ ID NO 34
<211> LENGTH: 24
<212> TYPE: DNA
<213> ORGANISM: Artificial Sequence
<220> FEATURE:
<223> OTHER INFORMATION: prIG23 primer

<400> SEQUENCE: 34
ggatccttaa tggtgatggt gatg                                             24

<210> SEQ ID NO 35
<211> LENGTH: 708
<212> TYPE: DNA
<213> ORGANISM: Artificial Sequence
```

```
<220> FEATURE:
<223> OTHER INFORMATION: IG5 Fusion Protein coding sequence

<400> SEQUENCE: 35
catatgttcg ttaaccagca tctgtgtggc tctcacctgg ttgaagccct gtatctggtt      60
tgcggtgaac gcggcttttt ctacaccccg aaaacccgtc gtgaagcgga agatctgcag    120
gtggggcagg tggagctggg cgggggccct ggtgcaggca gcctgcagcc cttggccctg    180 gagggtccc tgcagaagcg tggcactaac atgttcacct atgaaattgc tccagtattt    240
gtgcttttgg aatatgtcac actaaagaaa atgagagaaa tcattggctg ccagggggc    300 tctggcgatg gaggcggtat gaacattctg ctgcagtatg ttgttaaaag cttcgataac    360
atgtatgcca tgatgatcgc gcgctttaaa atgttcccgg aagttaaaga aaaaggtatg    420
gccgcgctgc cgcgtctggg aggcggtatt gcctttacct ctgaacatag ccattttttct   480 ctgaaaaaag gagctgcagc cttagggatt ggaacagaca gcgtgattgg aggcggttac    540
attcctccaa gcttgcgtac tctggaagac aatgaagaac gcatgagccg tctgtctaaa    600
gttgccccgg ttattaaagc gcgcatgatg aatatggca ccaccatggt tagctaccag     660
ccgctgggtg ataaagttaa ccaccatcac catcaccatt aaggatcc                  708

<210> SEQ ID NO 36
<211> LENGTH: 1191
<212> TYPE: DNA
<213> ORGANISM: Artificial Sequence
<220> FEATURE:
<223> OTHER INFORMATION: IG6 Fusion Protein coding sequence

<400> SEQUENCE: 36
catatgttcg ttaaccagca tctgtgtggc tctcacctgg ttgaagccct gtatctggtt      60
tgcggtgaac gcggcttttt ctacaccccg aaaacccgtc gtgaagcgga agatctgcag    120
gtggggcagg tggagctggg cgggggccct ggtgcaggca gcctgcagcc cttggccctg    180 gagggtccc tgcagaagcg tggcactaac atgttcacct atgaaattgc tccagtattt    240
gtgcttttgg aatatgtcac actaaagaaa atgagagaaa tcattggctg ccagggggc    300 tctggcgatg gaggcggtat gaacattctg ctgcagtatg ttgttaaaag cttcgataac    360
atgtatgcca tgatgatcgc gcgctttaaa atgttcccgg aagttaaaga aaaaggtatg    420
gccgcgctgc cgcgtctggg aggcggtatt gcctttacct ctgaacatag ccattttttct   480 ctgaaaaaag gagctgcagc cttagggatt ggaacagaca gcgtgattgg aggcggtatt   540
gagcatgacc ctcggatgcc agcctacata gccacgcagg gcccgctgtc ccataccatc    600
gcagacttct ggcagatggt gtgggagagc ggctgcaccg tcatcgtcat gctgaccccg    660
ctggtggagg atggtgtcaa gcagtgtgac cgctactggc cagatgaggg tgcctccctc    720
taccacgtat atgaggtgaa cctggtgtcg gagcacatct ggtgcgagga cttttctggtg   780 cggagcttct acctgaagaa cgtgcagacc caggagacgc gcacgctcac gcagttccac    840
ttcctcagct ggccggcaga gggcacaccg gcctccacgc ggcccctgct ggacttccgc    900
aggaaggtga acaagtgcta ccggggccgc tcctgcccca tcatcgtgca ctgcagtgat    960
ggtgcgggga ggaccggcac ctacatcctc atcgacatgg tcctgaaccg catggcaaaa   1020
ggagtgaagg agattgacat cgctgccacc ctggagcatg tccgtgacca gcggcctggc   1080
cttgtccgct ctaaggacca gtttgaattt gccctgacag ccgtggcgga ggaagtgaat   1140
gccatcctca aggccctgcc ccagcaccat caccatcacc attaaggatc c             1191
```

<210> SEQ ID NO 37
<211> LENGTH: 1344
<212> TYPE: DNA
<213> ORGANISM: Artificial Sequence
<220> FEATURE:
<223> OTHER INFORMATION: IG7 Fusion Protein coding sequence

<400> SEQUENCE: 37

| | | | | | |
|---|---|---|---|---|---|
| catatgttcg | ttaaccagca | tctgtgtggc | tctcacctgg | ttgaagccct | gtatctggtt | 60 |
| tgcggtgaac | gcggctttt | ctacaccccg | aaaacccgtc | gtgaagcgga | agatctgcag | 120 |
| gtggggcagg | tggagctggg | cggggcccct | ggtgcaggca | gcctgcagcc | cttggccctg | 180 |
| gagggggtccc | tgcagaagcg | tggcactaac | atgttcacct | atgaaattgc | tccagtattt | 240 |
| gtgcttttgg | aatatgtcac | actaaagaaa | atgagagaaa | tcattggctg | gccaggggc | 300 |
| tctggcgatg | gaggcggtat | gaacattctg | ctgcagtatg | ttgttaaaag | cttcgataac | 360 |
| atgtatgcca | tgatgatcgc | gcgctttaaa | atgttcccgg | aagttaaaga | aaaaggtatg | 420 |
| gccgcgctgc | cgcgtctggg | aggcggtatt | gcctttacct | ctgaacatag | ccattttct | 480 |
| ctgaaaaaag | gagctgcagc | cttagggatt | ggaacagaca | gcgtgattgg | aggcggttac | 540 |
| attcctccaa | gcttgcgtac | tctggaagac | aatgaagaac | gcatgagccg | tctgtctaaa | 600 |
| gttgccccgg | ttattaaagc | gcgcatgatg | gaatatggca | ccaccatggt | tagctaccag | 660 |
| ccgctgggtg | ataaagttaa | cggaggcggt | attgagcatg | accctcggat | gccagcctac | 720 |
| atagccacgc | agggcccgct | gtcccatacc | atcgcagact | tctggcagat | ggtgtgggag | 780 |
| agcggctgca | ccgtcatcgt | catgctgacc | ccgctggtgg | aggatggtgt | caagcagtgt | 840 |
| gaccgctact | ggccagatga | gggtgcctcc | ctctaccacg | tatatgaggt | gaacctggtg | 900 |
| tcggagcaca | tctggtgcga | ggactttctg | gtgcggagct | tctacctgaa | gaacgtgcag | 960 |
| acccaggaga | cgcgcacgct | cacgcagttc | cacttcctca | gctggccggc | agagggcaca | 1020 |
| ccggcctcca | cgcggcccct | gctggacttc | cgcaggaagg | tgaacaagtg | ctaccggggc | 1080 |
| cgctcctgcc | ccatcatcgt | gcactgcagt | gatggtgcgg | ggaggaccgg | cacctacatc | 1140 |
| ctcatcgaca | tggtcctgaa | ccgcatggca | aaaggagtga | aggagattga | catcgctgcc | 1200 |
| accctggagc | atgtccgtga | ccagcggcct | ggccttgtcc | gctctaagga | ccagtttgaa | 1260 |
| tttgccctga | cagccgtggc | ggaggaagtg | aatgccatcc | tcaaggccct | gccccagcac | 1320 |
| catcaccatc | accattaagg | atcc | | | | 1344 |

CHIMERIC PROTEINS FOR DIAGNOSIS AND TREATMENT OF DIABETES

CROSS REFERENCE TO RELATED APPLICATION

This application is a continuation of PCT/US98/27408, filed Dec. 23, 1998, which is a continuation of U.S. provisional application Ser. No. 60/068,648, filed Dec. 23, 1997, each of which is herein incorporated by reference.

BACKGROUND OF THE INVENTION

The discussion in this section is not limited to subject matter that qualifies as "prior art" against the present invention. Therefore, no admission of such prior art status shall be implied or inferred by reason of inclusion of particular subject matter in this discussion, and no declaration against the present inventors' interests shall be implied by reason of such inclusion.

Diabetes Mellitus

Diabetes mellitus is the most common endocrine disease, and is characterized by abnormalities of glucose metabolism. The abnormal glucose metabolism associated with this disease results in hyperglycemia (high blood glucose levels) and eventually causes complications of multiple organ systems, including eyes, kidneys, nerves, and blood vessels. Patients with persistent hyperglycemia or abnormal glucose tolerance are generally diagnosed with the disease, although most commonly patients initially present with excessive urination (polyuria) and frequent drinking due to extreme thirst (polydipsia). These typical initial symptoms result from the osmotic effects of hyperglycemia.

The pathogenesis of diabetes mellitus is typically associated with pancreatic dysfunction, particularly of the beta cells of the pancreatic islets of Langerhans. This dysfunction may lead to destruction of the islet beta cells, which produce insulin, a glucose regulatory peptide hormone. Diabetes mellitus has been generally categorized as insulin dependent or type 1, versus non-insulin dependent, or type 2. However, this terminology has evolved as the disease has become better understood. For example, it has been found that in some patients suffering from non-insulin dependent diabetes, the disease progresses into an insulin dependent form, while in other patients insulin dependence does not develop.

Patients are thus often categorized in terms of the mechanisms of pathogenesis of islet destruction, and the designation type 1 is now used to refer to autoimmune islet pathogenesis, i.e., to diabetes caused by islet-specific autoimmune attack, and is so used herein. The term insulin dependent diabetes mellitus (IDDM) refers to Type 1 diabetes that has progressed to a stage where enough autoimmune destruction of the pancreatic beta cells has occurred to produce overt symptoms. The term pre-IDDM refers to an autoimmune condition that can be detected by biopsy or by analysis of autoimmune responses, in which pancreatic islet beta cells are being subject to a specific autoimmune attack to an extent where some cells may be subject to destruction. In pre-IDDM, however, the destruction (if any) has not progressed to an extent sufficient to require the administration of insulin. Since there can be a point in the early stages of Type 1 diabetes in which overt symptoms are observed but some islet function remains (known as the "honeymoon period", not all Type 1 diabetes is classified as IDDM, and not all pre-IDDM presents without overt symptoms.

Complications of Type 1 Diabetes The metabolic complications associated with the abnormal metabolism caused by insulin insufficiency can affect numerous organ systems. The most common acute metabolic complication is that of diabetic ketoacidosis, characterized by severe hyperglycemia (and resulting hypovolemia caused by osmotic diuresis) as well as metabolic acidosis induced by excess free fatty acid release and the production of ketone bodies.

In addition to the acute metabolic complication of ketoacidosis, the diabetic patient is susceotible to a series of late complications that cause considerable morbidity and premature mortality. Atherosclerosis occurs more extensively and earlier in diabetics than in the general population as a result of abnormalities in both glucose and lipid metabolism. This vascular pathology can lead to, inter alia, coronary artery disease, stroke, and peripheral vascular disease with gangrene. Retinopathy is another vascular complication of diabetes. Diabetic retinopathy is a leading cause of blindness, and is initiated by increased permeability of retinal capillaries which can progress to occlusion, hemorrhage, aneurysm formation, and neovascularization known as proliferative retinopathy.

In addition to vascular complications, kidney and neurological diseases (nephropathies and neuropathies) are common complications of diabetes. Diabetic nephropathy causes about half of end-stage renal disease in the United States. Histologically, the nephropathy is characterized by glomerular basement membrane widening and mesangial thickening. Initial signs include increasing proteinuria, with azotemia ultimately leading to renal failure. Diabetic neuropathy can affect any part of the nervous system, with the possible exception of the brain. The neuropathy is most commonly seen as peripheral polyneuropathy, with symptoms including numbness, paresthesias, severe hyperesthesias, and pain. Autonomic neuropathy can cause gastrointestinal dysfunction, orthostatic hypotension, bladder dysfunction or paralysis, and impotence. Diabetic foot ulcers represent a special problem of diabetics, and appear to be due primarily to abnormal pressure distribution secondary to diabetic neuropathy. The ulcerous lesions are often worsened by concomitant peripheral vascular disease and infection.

As mentioned above, meticulous control of blood glucose has been associated with amelioration of the late complications of Type 1 diabetes, suggesting that that preservation or restoration of beta cell function could reduce or eliminate the majority of the pathologic complications of the disease.

Pathogenesis of Type 1 Diabetes Type 1 diabetes only develops in genetically susceptible individuals, and symptoms generally appear before age 40, with the peak incidence of onset of overt symptomology occurring in the second decade of life. The pathogenesis of Type 1 diabetes is characterized by an initial phase of leukocyte infiltration into the islets, referred to as insulitis, followed over a period of time by the actual destruction of the islet beta cells by autoimmune attack. The insulitis phase is characterized by infiltration of pancreatic islets by both lymphocytes and cells of the monocyte/macrophage lineage, and entails both cell-mediated inflammation as well as attack by islet-specific cytotoxic antibodies. Overt clinical symptoms of diabetes mellitus are generally manifested when over 90% of the islet beta cells are destroyed; however, as discussed more fully below, it is now possible to accurately detect individuals undergoing earlier stages of type 1 pathogenesis, i.e., before enough islet beta cells have been lost to produce overt clinical symptoms.

The autoimmune process is generally thought to be induced by an environmental stimulus. One reason for this belief is that an identical twin has only a fifty/fifty chance of developing IDDM if his identical sibling has the disease.

T Cells The autoimmune destruction of the beta cells of the pancreatic islets in Type 1 diabetes is believed to be initiated by white blood cells (leukocytes), most importantly T cells. T cells, or T-lymphocytes, are mononuclear white blood cells that provide many essential immune functions. The importance of T cells in human autoimmune diseases has been increasingly appreciated in the past two decades. Studies using treatments that result in generalized immunosuppression have defined a critical role for a subset of T cells, known as $CD4^+$ or helper T cells, as primary regulators of all immune responses (both cellular and humoral) to protein or peptide antigens.

T cells mediate tissue injury by indirect and direct means. T cells of both $CD8^+$ (cytotoxic) and $CD4^+$ (helper) subsets secrete a variety of inflammatory cytokines that can damage tissues indirectly by activating various other types of white blood cells. Examples of such T cell effects include activation of antibody secreting B cells (stimulating humoral immune activity) and activation of macrophages, which can cause acute tissue damage and inflammation by releasing hydrolytic enzymes, reactive oxygen species, and additional pro-inflammatory cytokines. In addition to these indirect effects of T cell activity, direct tissue damage can be mediated by $CD8^+$cytotoxic T cells attacking cells displaying target antigens.

One unique aspect of the physiology of T cells is the presence of membrane bound antibody-like binding structures called T cell receptors (TCRs) on their cell surfaces. Like antibodies, TCRs bind with high specificity to particular antigens. Like antibody-producing cells, which develop as multitudinous clones of cells, each clone producing antibodies with unique specificities, T cells develop as a vast number of distinct clones, and any particular T cell clone expresses a single type of TCR with a defined binding specificity. T cell clones with TCRs that bind specifically to self antigens are responsible for the development of autoimmune diseases.

Studies of the interactions of antibodies and TCRs with their specific antigens have shown that a particular polypeptide antigen typically comprises numerous submolecular features, known as epitopes, that each can serve as a distinct binding site for a particular antibody or TCR.

T Cells and Autoimmune Diseases In autoimmune diseases, only a limited number of T cell clones, reactive with various epitopes of a small number of autoantigens, become activated and are involved in pathogenesis. Even in individuals suffering from autoimmune diseases, only a small percentage of T cell clones (0.1–1%) are known to recognize autoantigens.

Various mechanisms have been postulated to play a role in the pathogenic activation of disease-causing autoreactive T cells. Primary activation of antigen presenting cells (APCs) by infection or local inflammation is implicated in one such mechanism. APCs activated in this way can then provide powerful co-stimulation for hitherto unreactive T cells.

Other proposed mechanisms involve the polyclonal activation of previously quiescent autoreactive T cells by superantigens, such as bacterial toxins; or a coincidental molecular mimicry between foreign and self antigens (Abbas et. al. 1994). In this last case, the host immune system mounts a response to an epitope on a protein expressed by a pathogen, such as a virus, that resembles a homologous epitope on a host protein. Autoimmune attack then results from the cross-reactive immune response that ensues.

In addition to external factors, underlying the emergence of all T cell-mediated autoimmune disease is a complex pattern of inherited susceptibility determined by multigenic factors. For further discussions of these various factors, Steinman, 1995, reviews current theories of autoimmunity.

Alterations in the T cell repertoire occur naturally during T cell development. Only a small fraction of thymocytes (immature T cells) survive the intrathymic development and selection events that result in emigration of developing T cells to the peripheral circulation and the completion of their maturation (von Boehmer, 1988; Marrack and Kappler, 1987). Experimental evidence strongly suggests that a large number of thymocytes that bear receptors for autoantigens are initially present in the thymus. Recent studies have yielded evidence suggesting that a process referred to as programmed cell death, or apoptosis, destroys these autoreactive thymocytes in the thymus while sparing thymocytes that are not autoreactive. Apoptosis thus plays a large role in shaping and maintaining the T cell repertoire and contributes to the establishment of self-tolerance by actively eliminating cells expressing autoreactive TCRs.

It has recently been discovered that T cells are sensitive to apoptotic cell death induced by a variety of stimuli at multiple points in their lifespan (see, for example, Lenardo 1991; Boehme and Lenardo 1993; Critchfield et al. 1994). Positive selection factors are also believed to play a role in regulating the survival of specific T cell clones. The reduction or expansion of the number of individual T cells of a particular clone in an organism by these and other mechanisms serve to modulate the responsiveness of the organism's immune system to a particular antigen. It is now firmly established in several autoimmune disease models, as well as in certain viral infections, that apoptosis can be induced (upon exposure to antigen under certain defined conditions) in mature peripheral antigen-specific T lymphocytes as well as in immature thymocytes.

Apoptosis occurs in many biological systems (see, for example, Kerr et al. 1991; Lockshin and Zakeri, 1991; Cohen et al. 1992; Duvall and Wyllie, 1986; Cotter et al. 1990). A cell undergoing apoptosis undergoes a specific program of events—cellular and biochemical processes that depend upon active metabolism and contribute to the cell's self-destruction. In apoptotic T cells, the nucleus shrinks, the chromatin condenses, the genetic material (DNA) progressively degrades into small (nucleosomal repeat sized) fragments, there is cytoplasmic compaction, the cell membrane forms blebs, and the cell eventually collapses (Kawabe and Ochi, 1991; Smith et al. 1989). Cells cannot recover from apoptosis, it results in irreversible cell death (Kawabe and Ochi, 1991; Smith et al. 1989).

Recent reports have suggested a role for the TNF-related cytokine known as the FAS ligand and its receptor, CD95 (the FAS receptor), in the induction of apoptosis in T cells (Crispe et al. 1994; Nagata and Suda, 1995; Strasser, 1995; Dhein et al., 1995; Brunner et al., 1995; and Ju et al., 1995).

Islet Beta Cell Autoantigens As discussed above, the onset of Type 1 diabetes is considered to be mediated by T cells. The disease is believed to be a consequence of inappropriate T cell responses specific to certain islet beta cell proteins that act as autoantigens. In addition to autoreactive T cells, autoantibodies against various self antigens have also been reported in IDDM patients. The antigens reported to be bound by these autoantibodies include many of those that have been reported to be recognized by autoreactive T cells.

Autoantigens that are subject to autoimmune responses in Type 1 patients include the 64–65 kDa GAD (glutamate decarboxylase) and the 67 kDa GAD autoantigens; insulin; sialyglycolipid; a 38 kD antigen from the secretory granules of beta cells; an antigen cross reactive with antibodies to bovine albumin known as the beta cell p69 protein, PM-1, or disease-modifying antigen, a beta cell cytoskeletal protein known as peripherin, glucose transporter proteins, including GLUT-2; heat shock protein 65 (HSP 65), including the p277 peptide; carboxypeptidase H; a 52 Kd molecular mimic of Rubella virus antigen; a beta cell membrane associated protein of 150 kDa; a protein antigen located at the secretory pole of the rat insulinoma cell line RINm38, referred to as the RIN polar antigen; and (at first) poorly characterized antigens isolated by immunoscreening of an islet cDNA expression library, referred to as ICA12 and ICA512. ICA512, now also known as IA-2, is immunologically related to phogrin, which is also subject to autoimmune responses in Type 1 patients (Hatfield et al., 1997).

The relative importance of these various autoantigens to autoimmune pathogenesis, and the timing with which each plays a role during the course of disease onset and development, are the subject of considerable uncertainty and consequent controversy in the art. Further uncertainty stems from the fact that each supposed autoantigen comprises numerous epitopes, some of which may be have disease promoting effects while others may have disease suppressive effects.

While not wishing to be bound by any particular theory of operation, in accordance with certain aspects of the invention insulin and GAD are believed to provide the most effective therapeutic effects on the development of Type 1 diabetes of any of the autoantigens implicated as playing a role in the pathogenesis of the disease. In accordance with certain other aspects of the invention, IA-2 is also believed to provide effective therapeutic effects.

Autoantibodies to 64–65 kD GAD (hereinafter GAD 65) normally are detected before the onset of clinical insulin dependent Type 1 diabetes mellitus, and among nondiabetic relatives of patients with IDDM as well as others at risk. These autoantibodies have been suggested to be the best predictive autoantibody marker for impending Type 1 diabetes.

GAD 65 and GAD 67 are encoded by different genes on different chromosomes, the genes being about 70% homologous. Human islets only express GAD 65, although both protein forms are found in the brain. Evidence of lymphocyte specific immunity to GAD 65 has been demonstrated and found to be closely associated with IDDM. Recent studies in the NOD mouse model of diabetes have indicated that T cell responses to GAD 65 precede those to other putative autoantigens and that early induction of T cell tolerance to GAD 65 can prevent onset of disease.

Kaufman et al (1993) and Tisch et al (1993) have presented data that suggest that GAD responses are the most important in disease development, as they were reported to arise first during the development of Type 1 diabetes, with responses to other beta cell autoantigens only appearing much later in the course of the disease, with insulin reactivity being amongst the last to appear. These findings were interpreted as indicating that GAD 65 is the key autoantigen in Type 1 diabetes, and that modulation of autoimmune reactivity with GAD would be the most appropriate target for reducing disease pathology. In accordance with this theoretical understanding of disease progression, modulation of insulin reactive T cells would be closing the barn door after the horses had gone, the anti-insulin reactions being observed so late in disease progression that their modulation would not be expected to affect the onset or severity of disease.

Insulin autoantibodies (IAA) can be detected in around 50% of new onset patients, and are highly associated with islet cell autoantibodies (ICA) and the HLA-DR4 phenotype. Other studies suggest that individuals with both ICA and IAA have a much higher risk for developing overt Type 1 diabetes than those with either marker alone. T cell responses to insulin as an autoantigen have also been described. In one study cellular responses to human insulin were present in almost 90% of ICA-positive first degree relatives of IDDM patients. Also, as discussed below in the examples, insulin reactive T cells from diabetic NOD mice can transfer diabetes to non-diabetic NOD mice.

Responses of T cells from Type 1 diabetes patients or from at-risk individuals to undefined islet cell preparations have suggested that T cells also respond to other islet cell antigens. These include a 38 kD antigen from the secretory granules of beta cells, and serum albumin. In addition, heat shock protein (HSP) 65 has been implicated as a T cell autoantigen based upon the finding that HSP-specific T cells transfer disease in NOD mice.

Carboxypeptidase H is a molecule found in islet secretory granules and is associated with the production of peptide hormones and neurotransmitters. It was identified as a potential islet autoantigen by the screening of cDNA expression libraries with sera from IDDM or pre-IDDM patients.

Several other putative islet cell antigens, such as ICA12 and ICA512, have also been identified by screening of cDNA expression libraries.

Intra-antigenic and inter-antigenic spread of autoreactivity ("epitope spreading") are related phenomena associated with autoimmune diseases in which additional epitopes within an antigen, or additional antigens within a target tissue, become targeted by autoreactive T cells during disease progression. Such antigen spreading has been observed during the course of the inflammatory autoimmune process in the murine models of experimental allergic encephalomyelitis (EAE) and insulin-dependent diabetes (Lehmann et al. 1992; McCarron et al. 1990; Kaufman et al. 1993; Tisch et al. 1993).

These findings of antigen/epitope spreading suggest that for a therapeutic treatment to provide effective immune tolerance to islet beta cell autoantigens, the treatment will need to target a heterogeneous population of specific autoreactive T cells. Therefore, in order for antigen administration to be maximally effective in the prevention and treatment of Type 1 diabetes, it is desirable that a plurality of the immunodominant epitopes of both insulin and GAD 65 be presented to the disease producing autoreactive T lymphocytes.

Prediction and Diagnosis of Type 1 Disease As discussed above, there is a genetic aspect to the incidence of Type 1 diabetes. Accordingly, genetic tests can identify certain individuals at increased risk of developing the disease (see, for example, Walston et al. 1995). Furthermore, individuals with a known family history of the disease can be monitored for early, preclinical signs of disease development, e.g., by monitoring levels of the autoantibodies and autoreactive T cells discussed herein.

Autoantibodies Among the autoantibodies known to be associated with Type 1 diabetes, those directed against GAD 65 are the ones that appear earliest and are present in the largest number of patients. Overall, recent studies have shown that over 80% of individuals with preclinical diabetes have GAD-specific autoantibodies. In this case an individual with preclinical disease is defined as a first degree relative of a Type 1 diabetes patient with ICA. The antigens identified by ICA are ill-defined, but together with IAA and GAD-specific autoantibodies, they yield a high predictive value for onset of diabetes in preclinical individuals. Interestingly, in actual early onset disease, the frequency of GAD-specific antibodies declines. This could be due to the fact that GAD 65 reactivity declines with beta cell destruction.

Prediction of Type 1 diabetes may also be facilitated by monitoring of the subject's blood sugar levels, preferably, in conjunction with the administration of a glucose tolerance test to the subject. Such procedures are preferably carried out in combination with the monitoring of titers of the subject's circulating IAA, ICA, and GAD autoantibodies.

In accordance with the present invention, the chimeric proteins of the invention are fusion proteins that may be used as antigenic substrates for the detection of circulating autoantibodies, particularly IAA and/or GAD 65 autoantibodies, in diagnostic assays such as Western blot, ELISA, RIA, ELISPOT, and the like.

T cells Assays for the detection of T cells with specific reactivities are well known in the art, and include the mixed lymphocyte reaction (MLR) and the ELISPOT assay. ELISPOT assays are described, for example in Taguchi et al., J Immunol Meth 1990, 128:65 and Sun et al., J Immunol 1991 146:1490. In accordance with the invention, the chimeric fusion proteins of the invention may be used as substrates in such assays for the detection and quantification of insulin reactive T cells and/or GAD 65 reactive T cells and/or IA-2 reactive T cells.

Current Methods for Prevention and Treatment of Type 1 Diabetes. While diabetes has been studied for centuries, only a few effective treatments are available for type 1 disease. The first line of treatment is diet, with appropriate caloric intake based on ideal body weight and a defined distribution among protein, glucose, and fat. However, in IDDM patients, the most important component of therapy is the administration of insulin, the goal of which is to maintain glucose levels as close to the normal range as possible throughout the day. Insulin is available in rapid, intermediate, and long-acting formulations which vary in onset, peak, and duration of action, and can be used in varying schedules of administration to attempt to optimally regulate plasma glucose levels.

Intensive insulin therapy refers to a rigorous regimen of administration of hormonally effective insulin and monitoring of blood sugar levels. This regimen is designed to control blood glucose as precisely as possible. The results of the multicenter Diabetes Control and Complication Trial established that complications of diabetes are significantly diminished by better control of blood glucose levels, and thus demonstrated the desirability of intensive insulin therapy. One problem with this approach is that intensive insulin therapy requires a high level of patient awareness and compliance, as well as a highly skilled care team of physicians, nurses, and dietitians. The goals of intensive insulin therapy are thus extremely difficult to achieve, even with motivated and educated patients. Another problem is that a higher rate of hypoglycemia is seen in such rigorously treated patients than in patients receiving standard, less rigorous, insulin regimens.

The Diabetes Control and Complication Trial highlighted not only the benefit to overall metabolic health of maintaining normal blood glucose levels, but also a fundamental problem associated with the treatment of Type 1 diabetes, namely that the overt symptoms of the disease are manifested only when essentially all of the patients' islets are destroyed. Oral agents for diabetes, such as the sulfonylureas, act primarily by stimulating the release of insulin from dysfunctional beta cells, and thus are not useful for most patients with type 1 disease, i.e. for those patients with IDDM.

A major goal in the treatment of diabetes has been to develop therapies capable of aborting the autoimmune attack on the islet beta cells prior to their complete destruction, thereby preserving enough endogenous function to maintain normal metabolic control.

Induction of tolerance In the NOD (non-obese diabetic) mouse model of diabetes, it has been shown that oral feeding of insulin delayed the onset and reduced the severity of the disease. The mechanism proposed to explain oral tolerance is that oral antigen administration induces populations of antigen-specific Th2 T cells that secrete antiinflammatory cytokines such as IL-4, IL-10, and TGF-beta. These T cells circulate and are activated to secrete cytokines only in the presence of their specific antigen. Thus, insulin-specific Th2 T cells would be activated only in the pancreas where they would produce suppressive cytokines to modulate the autoimmune process. This mechanism does not require, therefore, that the oral antigen actually represent a disease-specific autoantigen, but rather only that it is expressed in a tissue specific fashion.

In contrast, methods designed to produce T cell tolerance (e.g., by anergy or apoptosis) require the identification of the actual disease-specific autoantigens that are targeted by autoimmune attack. Such antigens are then administered to patients in an appropriate tolerizing fashion (which may also induce non-antigen-specific tolerizing effects). Given that Type 1 diabetes is in significant measure a disease mediated by islet-specific autoreactive T cells, therapy of this type should be feasible in principle. Thus, induction of neonatal tolerance to GAD 65, as referred to above, prevented onset of disease in NOD mice. In addition, injection of crude islet extracts intrathymically, where tolerization of developing T cells takes place, has also protected both NOD mice as well as pre-diabetic BB rats from developing clinical disease.

One approach taken to induce insulin tolerance involves the parenteral administration of insulin, in combination with a conventional adjuvant (e.g., Freund's adjuvant). Typically this approach involves the administration of doses of insulin that would not be large enough to be expected to cause insulin shock in the patient. Notably, the insulin moieties of the chimeric fusion proteins of the present invention are hormonally ineffective, and are thus suitable for use in accordance with the methods of U.S. application Ser. No. 08/565,769, filed in the name of Yi Wang, which is incorporated herein by reference.

Apoptosis Apoptosis is a form of programmed cell death that occurs in many biological systems (Kerr et al., 1991; Lockshin and Zakeri, 1991; Cohen et al., 1992; Duvall and Wyllie, 1986; Cotter et al., 1990). As discussed above, an apoptotic cell undergoes a specific program of events that depend upon active metabolism and contribute to its own self-destruction. T cells that do not undergo apoptosis, but which have become activated, will carry out their "effector" functions by causing cytolysis, or by secreting lymphokines that cause B cell responses or other immune effects (Paul, 1989, pp. 3–38). These "effector" functions are the cause of tissue damage in autoimmune and other diseases. A powerful approach to avoiding disease is thus to permanently eliminate by apoptosis only those T cells reactive with autoimmune disease-inciting antigens, while leaving the majority of the T cell repertoire intact. The use of autoantigens to carry out this approach is described in PCT patent publication No. 94/28926, filed in the name of Michael J. Lenardo, and entitled Interleukin-2 Stimulated T Lymphocyte Cell Death for the Treatment of Autoimmune Diseases, Allergic Disorders, and Graft Rejection, and PCT patent publication No. 94/03202, filed in the name of Michael J. Lenardo, Stefen A. Boehme, and Jeffrey Critchfield and entitled Interleukin-4 Stimulated T Lymphocyte Cell Death, both of which patent publications are incorporated herein by reference.

Transplantation Transplantation of healthy pancreata, pancreatic tissue, or isolated pancreatic islets into patients suffering from Type 1 diabetes provides an effective treatment modality. Unfortunately, the duration of the therapeutic benefit of such transplants is currently limited by the same autoimmune phenomena that cause type 1 disease in the first place. Accordingly, treatment of a diabetic patient using the chimeric fusion proteins of the invention in accordance with the methods of the present invention, when carried out prior to, concomitantly with, and/or shortly after such a transplant, will increase the longevity of such transplants and thereby enhance the therapeutic benefit of such transplantation procedures.

The accompanying figures, which are incorporated in and constitute part of the specification, illustrate certain aspects of the invention, and together with the description, serve to explain the principles of the invention. It is to be understood, of course, that both the figures and the description are explanatory only and are not restrictive of the invention.

BRIEF DESCRIPTION OF THE DRAWINGS

FIG. 2 shows the results of CYTOXAN induced IDDM experiments in which NOD mice were treated with bovine serum albumin (BSA, as control) insulin chain B (ICB) human GAD 65 peptide 250–273, or human GAD 65 peptide 520–555 (a peptide with a sequence corresponding to amino acid residues 139–173 of SEQ ID NO:2).

SUMMARY OF THE INVENTION

Figure 1A:
FIG. 1A shows a schematic diagram of the IG1 fusion protein (SEQ ID NO:1). The numbers following the backslashes in the legend indicate the GAD 65 peptide moiety to which region corresponds. For hGAD 65/473-5---, 5--- indicates 555.
Figure 1B:
FIG. 1B shows a schematic diagram of the IG2 fusion protein (SEQ ID NO:2). The numbers following the backslashes in the legend indicate the GAD 65 peptide moiety to which region corresponds. For hGAD 65/473-5---, 5--- indicates 555.
Figure 1C:
FIG. 1C shows a schematic diagram of the IG3 fusion protein (SEQ ID NO:3). The numbers following the backslashes in the legend indicate the GAD 65 peptide moiety to which region corresponds. For hGAD 65/473-5---, 5--- indicates 519.

In view of the foregoing, the objects of this invention include the provision of novel chimeric fusion proteins that act as single molecular entities that 1)facilitate diagnosis and prognostic evaluation of individuals suspected of predisposition for the development of IDDM, as well as those suffering from IDDM and/or Stiff-Man syndrome, and 2)to provide enhanced beneficial effects when administered to animals (including human patients) suffering from or at risk of developing autoimmune (Type 1) diabetes. To these ends the invention provides chimeric fusion proteins comprising epitopes of both GAD (glutamate decarboxylase) and insulin. Preferably the GAD is GAD 65 and the GAD and insulin are human GAD and insulin.

In accordance with the invention, the combination of GAD 65 and insulin peptides in a single fusion protein provides a more convenient diagnostic reagent for the detection and prognostic evaluation of diabetes or stiff man syndrome. Discussion of Stiff-Man syndrome may be found, for example in U.S. Pat. No. 5,691,448, which is incorporated herein by reference.

In accordance with the invention, (and as set forth in the examples, below) the combination of GAD 65 and insulin chains and/or peptides in a single chimeric fusion protein further provides a compound which can be administered so as to furnish more effective immunomodulatory therapeutic treatment than the combination of the same peptides and/or insulin chains as discrete individual peptide moieties and insulin chains. More specifically, preferred chimeric fusion proteins of the invention, when tested in an assay in a mouse model of IDDM, provide a greater reduction in the frequency of onset of diabetes than a control mixture containing equimolar amounts of each of the various discrete individual peptide moieties and insulin chains comprised by the chimeric fusion protein, each of said individual peptide moieties and insulin chains not being covalently bound to any other of said individual peptide moieties and insulin chains in said mixture, wherein the assay is carried out by the repeated parenteral administration of a number of measured doses, each dose being of a predetermined molar quantity of said chimeric fusion protein in a pharmaceutically effective carrier or of said control mixture in the pharmaceutically effective carrier, the administration being at intervals of not less than twelve hours and not more than 72 hours between each of the doses.

As used herein, the phrase "the same peptides and insulin chains as discrete individual peptide moieties," used in comparison to a particular chimeric fusion protein of the invention, indicates a combination of isolated peptides and insulin chains that are not covalently linked together (e.g., by peptide bonds), wherein linking (via peptide bonds) the peptides and insulin chains together in the appropriate order (e.g., the same relative position in the amino terminal to carboxyl terminal sequence as found in full length GAD 65 and full length insulin chains) would produce the particular chimeric fusion protein of the invention.

While not wishing to be bound by any particular theory of operation, it is believed that complex in vivo antigen processing and presentation effects are responsible for the unexpected synergistic effects resulting from combining GAD 65 and insulin peptides and/or polypeptides into a single chimeric fusion protein.

The chimeric fusion proteins of the invention each combine in a single molecular entity the key (immunodominant) autoantigenic epitopes of both insulin and GAD 65. In so doing, they provide single component diagnostic and therapeutic compounds. The chimeric fusion proteins of the invention provide enhanced beneficial effects after administration to animals (including human patients) when compared to the administration of combinations of the individual peptides representing the same immunodominant epitopes as are comprised within the chimeric fusion proteins.

The preferred chimeric fusion proteins of the invention comprise insulin chain B (e.g., amino acids 1–31 of human insulin) and preferably further comprise insulin chain C (the "C fragment", e.g., amino acids 32–38 of human insulin). Amino acid sequences of insulin chains are known. See, for example, U.S. Pat. No. 4,431,740, which is incorporated herein by reference for the description of insulin chains and the content of the insulin sequences therein. See also U.S. Pat. No. 5,008,241, which is incorporated herein for its descriptions and sequences of insulin analogues, which analogues may be substituted for naturally occurring insulin chains in the chimeric fusion proteins of the present invention.

The chimeric fusion proteins of the invention further comprise at least one GAD peptide (i.e., polypeptide polymers of at least ten contiguous amino acids having a sequence identical to a contiguous sequence of at least ten amino acids found in GAD) that is covalently linked (preferably by peptide bonds) to the insulin chain, chains, analogues or peptides.

In accordance with the invention, the at least one GAD peptide is a GAD 65 peptide (i.e., a GAD peptide wherein the contiguous sequence of at least ten amino acids found in GAD is found in GAD 65). Preferably the GAD 65 peptide is a human GAD 65 peptide. Preferably the GAD 65 peptide is selected from the group consisting of human GAD 65 peptides 115–127 (a peptide corresponding to amino acid residues 39–50 of SEQ ID NO:2), 247–286 (a peptide corresponding to amino acid residues 51–90 of SEQ ID NO:2), and 473–519 (a peptide corresponding to amino acid residues 92–144 of SEQ ID NO:2). Complete amino acid sequences of GAD 65 polypeptides are known. See, for example, U.S. Pat. No. 5,691,448, which is incorporated herein by reference, particularly for the content of the sequence listings therein.

Results of studies described below suggest that the inclusion of human GAD 65 peptide 520–555 (a peptide with an amino acid sequence corresponding to amino acid residues 139–173 of SEQ ID NO:2) has a deleterious effect upon the immunomodulatory outcome of administration of insulin and GAD proteins or peptides. Accordingly, while within the scope of the invention, chimeric fusion proteins comprising human GAD 65 peptide 520–555 are disfavored. Preferably, the chimeric fusion proteins of the invention do not comprise a peptide sequence corresponding to GAD 65 peptide 520–555. It is also preferred that the chimeric fusion proteins of the invention do not include peptide sequences corresponding to those human GAD 65 peptides (particularly those amino terminal GAD 65 peptides) identified as inhibiting GAD solubility in U.S. Pat. No. 5,691,448 (which is incorporated herein by reference, particularly for its teachings in this regard) and do not contain peptide regions of GAD 65 that are associated with the pathogenesis of Stiff-Man syndrome. Thus, in accordance with the teachings of Butler et al., 1993, regarding dominant epitopes of GAD recognized by autoantibodies in Stiff-Man syndrome, the preferred chimeric fusion proteins of the invention do not include peptide regions comprising amino acids 1–95 of GAD 65; additionally, they do not include peptide regions comprising either or both of amino acids 475–484 or 571–585 of GAD 65.

Preferably the GAD peptides are arranged adjacently to each other (i.e., without more than about three intervening amino acids between them) in the same order as they are found in GAD 65, and the insulin chains are arranged adjacently to each other in the same order as they are found in preproinsulin. An arrangement where the insulin chains are amino terminal to the GAD peptides is also preferred in certain embodiments of the invention.

In certain preferred embodiments of the invention, at least one (preferably each) of the cysteine residues in the amino acid sequences of the various antigens and antigenic peptides combined to form the chimeric fusion proteins of the invention is replaced with an uncharged amino acid (i.e., an amino acid that is uncharged at a pH of between 6 and 7) having a molecular weight of less than about 150. In another preferred embodiment, none of such cysteine residues are replaced, i.e., there are no substitutions made for any cysteine residues present in any of the various antigens and antigenic peptides combined to form the chimeric fusion protein. When cysteine residues are replaced, the uncharged amino acid is preferably a standard amino acid. Preferably the standard amino acid is alanine or serine. Preferably the replacement of cysteine with another neutral amino acid is an epitope neutral replacement, i.e., it does not result in epitope conversion in any of the known immunodominant epitopes of the chimeric fusion protein, particularly those of GAD or insulin.

Detailed discussions of epitope neutral replacements and epitope conversion can be found in copending U.S. application Ser. No. 08/431,644, filed May 2, 1995 in the names of Steven H. Nye et al., for example at pages 34–36 of the specification of that application as filed. Also see copending U.S. patent application Ser. No. 08/482,114, filed Jun. 7, 1995 in the names of John P. Mueller et al. Those of skill in the art will readily comprehend the application of the teachings therein to the chimeric fusion proteins of the present invention. Accordingly, copending U.S. patent application Ser. Nos. 08/431,644 and 08/482,114 are incorporated herein by reference to more fully describe the epitope neutral amino acid replacements encompassed within the chimeric fusion proteins of the present invention.

It is a further object to provide immunomodulatory methods for both the prevention and treatment of Type 1 diabetes mellitus and the amelioration of the autoimmune defects underlying this disease. Accordingly, it is an additional object of the invention to provide for the use of the chimeric fusion proteins of the invention in the manufacture of immunomodulatory medicaments.

To achieve these and other objects, the invention provides methods of treating a patient in need of such treatment, e.g., a patient selected from the group of patients consisting of patients at risk of developing type 1 diabetes and patients suffering from type 1 diabetes, so as to delay the onset or reduce the symptoms of diabetes in the patient and/or to ameliorate the autoimmune destruction of pancreatic beta cells in treated patients. Such treatment is particularly advantageous, and is preferably carried out, during the "honeymoon period" early in disease progression, before all of the patient's beta cells have been destroyed by the disease, or later in disease progression, when a patient is a candidate for transplantation of islet cells or tissues containing such cells.

These methods comprise the administration of at least one polypeptide of the invention to the patient. In one preferred embodiment, such administration is carried out on a therapeutic T cell modulatory schedule, i.e., a schedule designed to induce apoptosis, anergy, or other modulation of the autoimmune activity of T cells reactive with at least one epitome of the at least one polypeptide. Particulars of such therapeutic T cell modulatory schedules are discussed below. Other preferred methods of treatment of the invention include administration of at least one polypeptide of the invention to the patient via oral, intravenous, or, preferably, subcutaneous routes, or via parenteral administration with or preferably without an adjuvant such as Freund's incomplete adjuvant, Freund's complete adjuvant, alum adjuvant, or other immunogenic adjuvants now known or subsequently developed.

DETAILED DESCRIPTION OF THE PREFERRED EMBODIMENTS

Chimeric fusion proteins All polypeptides synthesized in biological systems are initially made with an N-terminal methionine residue. The extreme N-terminal and C-terminal amino acid residues are not considered essential to the functional use of the polypeptides of the invention, which, although not particularly preferred, may be produced without such residues. For example, the polypeptides may be chemically synthesized without N-terminal methionines. Preferred chimeric proteins of the invention thus include IG1 (comprising amino acid residues starting at about residue 2 and ending at about residue 153 of SEQ ID NO:1), IG2 (comprising amino acid residues starting at about residue 2 and ending at about residue 173 of SEQ ID NO:2), IG3 (comprising amino acid residues starting at about residue 2 and ending at about residue 137 of SEQ ID NO:3), IG4 (comprising amino acid residues starting at about residue 2 and ending at about residue 175 of SEQ ID NO:4), IG5 (comprising amino acid residues starting at about residue 2 and ending at about residue 226 of SEQ ID NO:5), IG6 (comprising amino acid residues starting at about residue 2 and ending at about residue 387 of SEQ ID NO:6) and IG7 (comprising amino acid residues starting at about residue 2 and ending at about residue 439 of SEQ ID NO:7). Preferably IG1 comprises amino acid residues 1–154 of SEQ ID NO:1, IG2 comprises amino acid residues 1–174 of SEQ ID NO:2, IG3 comprises amino acid residues 1–138 of SEQ ID NO:3, IG4 comprises amino acid residues 1–175 of SEQ ID NO:4, IG5 comprises amino acid residues 1–226 of SEQ ID NO:5, IG6 comprises amino acid residues 1–387 of SEQ ID NO:6, and IG7 comprises amino acid residues 1–438 of SEQ ID NO:7.

In certain preferred embodiments these chimeric proteins further comprise a histidine tag (i.e., a stretch of at least five and preferably six contiguous histidine residues, which facilitates the purification of the chimeric fusion protein by metal chelation chromatography). Preferably the histidine tag is located at the extreme C-terminus of the chimeric fusion protein. Histidine tags are discussed in greater detail in copending U.S. patent application Ser. Nos. 08/431,644 and 08/482,114, which are incorporated herein by reference to more fully describe such histidine tag sequences and their uses.

Accordingly, in certain of these preferred embodiments IG1 comprises amino acid residues 1–160 of SEQ ID NO:1 and has a predicted molecular weight of about 18.8 kDa, IG2 comprises amino acid residues 1–180 of SEQ ID NO:2 and has a predicted molecular weight of about 21.2 kDa, IG3 comprises amino acid residues 1–144 of SEQ ID NO:3 and has a predicted molecular weight of about 17.1 kDa, IG4 comprises amino acid residues 1–181 of SEQ ID NO:4 and has a predicted molecular weight of about 19.8 kDa, IG5 comprises amino acid residues 1–232 of SEQ ID NO:5 and has a predicted molecular weight of about 25.3 kDa, IG6 comprises amino acid residues 1–393 of SEQ ID NO:6 and has a predicted molecular weight of about 43.7 kDa, and IG7 comprises amino acid residues 1–444 of SEQ ID NO:7 and has a predicted molecular weight of about 49.2 kDa.

Secondary Structure Considerations In designing IG4 (SEQ ID NO:4), IG5 (SEQ ID NO:5), and IG6 (SEQ ID NO:6), particular attention was paid to the predicted secondary structures of the polypeptides of the invention. IG4 was initially designed by hypothetically joining peptide epitopes of interest to form a single hypothetical sequence, IG4NHB (SEQ ID NO:8).

Secondary structure prediction of IG4NHB (SEQ ID NO:8) according to Chou and Fasman, 1978; Chou 1990; and Garnier et al., 1978; was performed using LASERGENE sequence analysis software (DNASTAR, Madison Wis.). This algorithm predicts secondary structure of proteins from their amino acid sequences. Other sequence analysis software may also be used for this purpose, including other commercially available software such as GCG or MACVECTOR.

The entire sequence from amino acid 77 (Phe 77) to amino acid 134 (Thr 134) of IG4NHB (SEQ ID NO:8) was predicted to have helix forming characteristics. The propensity for actual long helix formation diminishes very rapidly for sequences higher than 20 amino acids, with the longest unbroken helices typically containing no more than 26 amino acids. The 57 amino acid helix-forming sequence from amino acid 77 to 134 of IG4NHB (SEQ ID NO:8) would thus be expected to break at unpredictable, if not random, points so as to form a variety of different structures. Such structures are undesirable in the chimeric fusion proteins of the invention, as they would be likely to be prone to uncontrollable aggregation and would be expected to differ from the native secondary structures of the epitopes in the isolated peptides comprised by the chimeric fusion proteins of the invention and in the native proteins from which the peptides are derived (e.g., insulin, GAD 65, or IA-2), which native secondary structures are preferred for the epitopes contained within the chimeric fusion proteins of the invention. Therefore, in certain preferred embodiments of the invention, helix breakers (see following paragraph) are inserted between the epitopes to 1) block the formation of a very long helix and 2) to predictably separate the epitopes into distinct structural entities with distinct secondary structures.

Helix breakers are amino acids, or groups of sequential amino acids that act to block the propagation of helical secondary structures in nascent polypeptide chains. Gly and Pro are known to be strong helix breakers, Asn and Tyr are weak helix breakers. The insertion of any of these amino acids or combinations thereof in a polypeptide will tend to cause a nascent polypeptide secondary structure helix to terminate at the point of the insertion. To assure helix termination and the separation of the desired epitopes, a helix breaker that is at least two amino acids long (wherein each of the amino acids is the same or different from the other and is selected from the group consisting of Gly, Pro, Asn, and Tyr) is preferred, more preferably, such a helix breaker is at least three amino acids long. Most preferably, the helix breaker is exactly three amino acids long. Highly preferred helix breakers are Pro-Pro-Pro (SEQ ID NO:9) and Gly-Gly-Gly (SEQ ID NO:10), with the latter being the most preferred of these.

Dosage In accordance with the present invention, when used as therapeutic agents, the chimeric proteins of the invention are administered to patients in need of such treatment in amounts ranging from about 6.9 pM/kg/patient to about 8.6 µM/kg/patient. Preferably the amounts range from about 34.5 pM/kg/patient to about 5.2 µM/kg/patient. More preferably the amounts range from about 170 pM/kg/patient to about 3.5 µM/kg/patient. Most preferably the amounts range from about 0.5 µM/kg/patient to about 3.5 µM/kg/patient.

In certain of its aspects, the present invention also provides for the repeated administration of doses containing lower amounts of the chimeric fusion proteins of the invention to a patient in need of such treatment. Although less preferred, doses containing amounts of below about 6.9 pM/kg/patient, and as low as about 1 pM/kg/patient may be used in the practice of the present invention.

Preferably the chimeric proteins are administered without the concomitant administration of an adjuvant, however, when used to perform T cell assays (e.g., in transgenic mice such as described in Wong et al. 1998), initial administration to experimental animals is preferably made with adjuvant.

Administration on Therapeutic T Cell Modulatory Schedules In accordance with the invention, a therapeutic T cell modulatory schedule involves administration of doses containing the chimeric proteins of the invention, preferably in a pharmaceutically effective carrier, repeatedly to the patient, at least two times at an interval of at least six, and preferably at least twelve hours, with an interval of not more than seven days, preferably not more than 72 hours, more preferably not more than 48 hours, and most preferably not more than 24 hours between doses.

In accordance with the present invention, the chimeric fusion proteins of the invention are preferably administered parenterally without the concomitant administration of an adjuvant. Administration by a parenteral route will typically be via injection such as intravascular injection (e.g., intravenous infusion), subcutaneous injection, or intramuscular injection. Other non-oral routes of administration, e.g., mucosal, inhalation, transdermal ultrasound, and the like, may be used if desired and practicable for the particular polypeptide to be administered.

Although less preferred, the chimeric fusion proteins of the invention may also be administered orally, however dosages for oral administration will typically be one to two orders of magnitude higher that those discussed above under the sub-heading "Dosage."

Formulations suitable for injection and other routes of administration are well known in the art and may be found, for example, in *Remington's Pharmaceutical Sciences*, Mack Publishing Company, Philadelphia, Pa., 17th ed. (1985). Preferred formulations for parenteral administration of the proteins of the invention are those described for insulin in the USP 23/NF 18 (1995).

Parenteral formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. Formulations may also contain pharmaceutically acceptable auxiliary substances as required, such as, tonicity adjusting agents, wetting agents, bactericidal agents, preservatives, stabilizers, and the like.

Further discussions of dosage and administration of polypeptides using therapeutic T cell modulatory schedules may be found in copending U.S. patent application Ser. Nos. 08/431,644 and 08/482,114 (discussed above) and copending U.S. patent application Ser. No. 08/565,769, filed Dec. 1, 1995 in the name of Yi Wang, each of which is hereby incorporated herein by reference in its entirety to more fully describe the state of the art to which the present invention pertains.

Without intending to limit it in any manner, the present invention will be more fully described by the following examples.

Experimental Methods Non-obese diabetic (NOD) mice are a strain of mice that are prone to the development of diabetes, and represent an accepted model system for the study of diabetes mellitus. These mice, designated NOD/MrkTacfBR, were purchased from Taconic Farms (Germantown, N.Y.). NOD SCID mice, designated NOD/SCID, are available from the Jackson Laboratories, Bar Harbor, Me. The incidence of diabetes by 200 days of age in these mice is 80% in females and 50% in males. At 110 days of age, fewer than 15% of the male NOD mice became diabetic.

CYTOXAN induction experiments: CYTOXAN (Cyclophosphamide) treatment can increase the incidence and accelerate the onset of diabetes in non-diabetic NOD mice. Randomly selected, non-diabetic male NOD mice, which were 100 to 110 days of age, were injected (ip) with cyclophosphamide (250 mg/kg) on day 0.

All the mice were subjected to urine glucose measurement 2–3 times per week for a period of 21 days after cyclophosphamide injection. The onset of diabetes was recorded as the first point at which two consecutive days of positive urine glucose results were obtained. Blood glucose was also measured to confirm the urine glucose results. (ExacTech, MediSense Inc., Cambridge, Mass.) In all the mice tested with positive urine glucose, blood glucose levels were greater than 150 mg/dl. At day 21, these mice were sacrificed and examined histologically.

Experiments in the NOD/SCID Adoptive Transfer Model: Spleen mononuclear cells were harvested from diabetic NOD mice of recent disease onset (diabetic not more than 3 weeks) and about $35 \times 10^6$ of these spleen cells in 0.2 ml of PBS were injected intravenously into 6–8 week old NOD/SCID mice. Onset of diabetes was monitored biweekly by urine glucose testing and confirmed by blood glucose testing on day 28 relative to the time of spleen cell transfer. At day 28, these mice were sacrificed and examined histologically.

Reagents: CYTOXAN (cyclophosphamide, Mead Johnson oncology products) was dissolved in distilled water (25 mg/ml). Oxidized bovine insulin Chain B was purchased from Sigma (catalog no. I-6383). Both insulin chain B and the BSA control protein (Miles Inc., #81-001) were dissolved in PBS/1M HCL, pH2, before dialysis against PBS, pH7.2, sterile filtration, and storage of frozen aliquots.

EXAMPLES

Genes for Expression of Chimeric Proteins of the Invention

IG1. A synthetic chimeric gene encoding chimeric protein IG1 (SEQ ID NO:1) was constructed in two rounds of overlapping PCR (Ho et al., 1989). Each gene subdomain was synthesized in a standard PCR 100 μl reaction using 10 pmole of each of the appropriate oligonucleotide primers, as described below. The 5' gene segment was amplified using the overlapping primers:prIG1 (SEQ ID NO:11), and prIG2 (SEQ ID NO:12). The 3' gene segment was amplified using the overlapping primers prIG3 (SEQ ID NO:13) and prIG4 (SEQ ID NO:14). The prIG1 oligo-nucleotide (SEQ ID NO:11) was designed to allow creation of a unique NdeI restriction site at the 5' end. The prIG4 primer (SEQ ID NO:14)included a unique BamHI site, stop codon (TAA) and 18 nucleotides that encoded a histidine tag sequence for purification of the recombinant chimeric protein by metal affinity chromatography. The two subdomains were combined using flanking oligonucleotides prIG5 (SEQ ID NO:15) and prIG6 (SEQ ID NO:16) in a second PCR reaction to yield a 492 bp gene product. The PCR product was cloned into expression plasmid vector pCR2.1 as described by the supplier (Invitrogen, San Diego, Calif.). Kanamycin-resistant DH10B transformants were selected and the correct clones and orientations determined by restriction and sequence analysis. Restriction fragments from two clones (#6 and #18) were combined to remove undesired mutations. Following nucleotide sequence analysis, an independent plasmid pCR2.1-IG1 was digested with NdeI and BamHI and the 492 bp fragment inserted into compatible sites of the MP4 expression plasmid pET22b-MP4 (Elliott et al., 1996), yielding plasmid pIG1. The insert from pCR2.1-IG1 was also subcloned into plasmid vector pBLUSCRIPT®SK+ (STRATAGENE CLONING SYSTEMS, La Jolla, Calif.) to yield plasmid pSK+IG1. The synthetic IG1 gene (SEQ ID NO:17) encodes a chimeric fusion protein with a predicted mass of about 18.8 kDa.

IG2. A synthetic chimeric gene encoding chimeric protein IG2 (SEQ ID NO:2) was constructed by PCR amplification of an internal IG1 gene fragment using pIG1 as a template along with the sense primer prIG7 (5'-AGATCTGATG AACATTCTGC TGCAGTATGT TGTTAAAAGC TTC-GATAACA TGTATGCCAT GATG-3'—SEQ ID NO:18; BglII site underlined) in combination with the anti-sense oligonucleotide primer prIG8 (5'-TGTACAGATA TTC-CGCCAGT TCCAGACATT TTTTCAGAGA AAAATG-GCTA TGTTCAGAGG TAAAGGCAAT CAGACGCG-3'—SEQ ID NO:19; BsrG1 site underlined). The 197 bp BglII-BsrG1 PCR fragment was subcloned into pCR2.1. Sequence analysis revealed a C>G substitution at position 183 in the coding strand of the 197 bp BglII-BsrG1 PCR fragment for all subclones analyzed, and the plasmid was named pCR2.1-IG7/8C183G. Subsequent analysis revealed an error in the original prIG8 primer sequence (SEQ ID NO:19). A repair primer, prIG12 (SEQ ID NO:20), was synthesized to correct the C>G substitution in pCR2.1-IG7/8C183G. The internal 197 bp BglII-BsrG1 DNA segment was corrected by PCR using pCR2.1-IG7/8C183G as a template along with primers prIG7 (SEQ ID NO:18) and prIG12 (SEQ ID NO:20) The PCR fragments were subcloned into pCR2.1, their sequence was determined using standard dideoxy sequencing to confirm that the desired sequence had been obtained, and a single clone designated pCR2.1-IG7/12 was isolated and amplified.

The 137 bp BglII-BsrG1 restriction fragment in pSK+IG1 was exchanged with the 197 bp BglII-BsrG1 fragment from pCR2.1-IG7/12 to create pSK+/IG7/12. The 552 bp NdeI-BamHI fragment from pSK+/IG7/12 was subcloned into the compatible sites of pIG1 to create plasmid pIG2. The synthetic IG2 gene (SEQ ID NO:21) encodes a chimeric fusion protein with a predicted mass of about 21.2 kDa.

IG3. A synthetic chimeric gene encoding chimeric protein IG3 (SEQ ID NO:3) was constructed by removing a 552 bp NdeI-BamHI restriction fragment from plasmid pET22b-IG2 and substituting an NdeI-BamHI digested 444 base pair PCR product therefor. This 444 base pair PCR product was made using primers prIG5 (SEQ ID NO:15) and prIG13 (SEQ ID NO:22) with the synthetic IG2 gene as a template. The synthetic IG3 gene (SEQ ID NO:23) encodes a chimeric fusion protein with a predicted mass of about 17.1 kDa.

IG4. A gene sequence encoding chimeric protein IG4 (SEQ ID NO:4) is set forth below as SEQ ID NO:24, and encodes a chimeric fusion protein with a predicted mass of about 19.8 kDa.

IG5. A synthetic chimeric gene encoding chimeric protein IG5 (SEQ ID NO:5) was constructed via ligation of PCR products using primers prIG14 (SEQ ID NO:25), prIG15 (SEQ ID NO:26), prIG16 (SEQ ID NO:27), prIG17 (SEQ ID NO:28), prIG18 (SEQ ID NO:29), prIG19 (SEQ ID NO:30), prIG20 (SEQ ID NO:31), prIG21 (SEQ ID NO:32), prIG22 (SEQ ID NO:33), and prIG23 (SEQ ID NO:34). The synthetic IG5 gene (SEQ ID NO:35) encodes a chimeric fusion protein with a predicted mass of about 25.3 kDa.

IG6. A gene sequence encoding chimeric protein IG6 (SEQ ID NO:6) is set forth below as SEQ ID NO:36, and encodes a chimeric fusion protein with a predicted mass of about 43.7 kDa.

IG7. A gene sequence encoding chimeric protein IG7 (SEQ ID NO:7) is set forth below as SEQ ID NO:37, and encodes a chimeric fusion protein with a predicted mass of about 49.2 kDa.

Expression and purification of recombinant IG fusion proteins. For each IG fusion protein expression plasmid construction that was bacterially expressed, electrocompetent *E. coli* strain BL21(DE3) was transformed with the expression plasmid and ampicillin-resistant colonies were selected for liquid culture. The 1DE3 lysogen in strain BL21(DE3) contains the gene for T7 polymerase behind the *E. coli* lacUV5 promoter for efficient expression of target genes under control of the strong bacteriophage T7 transcriptional and translation signals (Studier et al., 1990).

The recombinant chimeric fusion protein was purified from solubilized whole cell pellets by immobilized metal affinity chromatography and analyzed by SDS-PAGE/

Coomassie blue staining. Four liters cultures were grown to $OD_{600}$ of 0.8 in Terrific Broth (TB) medium (Sambrook et al., 1992). Protein expression was induced for 5 hours with 1 mM isopropylthiogalactoside (IPTG). Induced cells were harvested by centrifugation and frozen overnight at −20° C. Cell pellets were thawed at room temperature and homogenized in 10 ml/g of Buffer A (6 M guanidine-HCl/10% glycerol/20 mM Tris-Cl pH 7.8/500 mM NaCl/200 mg sodium sulfite/280 mg sodium tetrathionate) using a TEK-MAR homogenizer (The Tekmar Co., Cincinnati, Ohio). Cells were frozen at −70° C. for 1 hour and thawed at room temperature to promote cell lysis. The cell suspension was gently mixed for 30 min at room temperature using a magnetic stirrer. The soluble fraction containing IG protein was collected as the supernatant following centrifugation of the cell lysate at 10,000×g for 30 min at 4° C. in a Beckman JA-10 rotor. The supernatant was loaded on a Ni-NTA (QIAGEN Inc., Chadsworth, Calif.) column previously equilibrated in Buffer A at a flow rate of 8 ml/min. The column was washed to baseline absorbance using Buffer A. The column was further washed with Buffer B (6 M urea/10% glycerol/20 mM Tris-Cl/500 mM NaCl pH 7.8) and contaminating *E. coli* proteins were removed with Buffer C (6 M urea/10% glycerol/20 mM Tris-Cl/500 mM NaCl pH 5.0). IG protein was eluted with Buffer D (6 M urea/10% glycerol/20 mM Tris-Cl/500 mM NaCl pH 4.0). All fractions were collected in batch and analyzed on a 4–20% SDS-polyacrlyamide gradient gel in the presence of reductant. The IG containing fractions (Buffer D wash) were concentrated 10-fold using an AMICON STIRCELL using a PM10 membrane. The sample was dialyzed against two changes of MILLI-Q water at 4° C. The IG preparations were filter sterilized and the concentration determined spectrophotometrically using a conversion factor of 1.06 mg/ml/$OD_{280}$. Five micrograms were analyzed under reducing and nonreducing conditions by SDS-PACE so as to obtain an initial indication of purify and integrity of the protein preparations.

Figure 3:
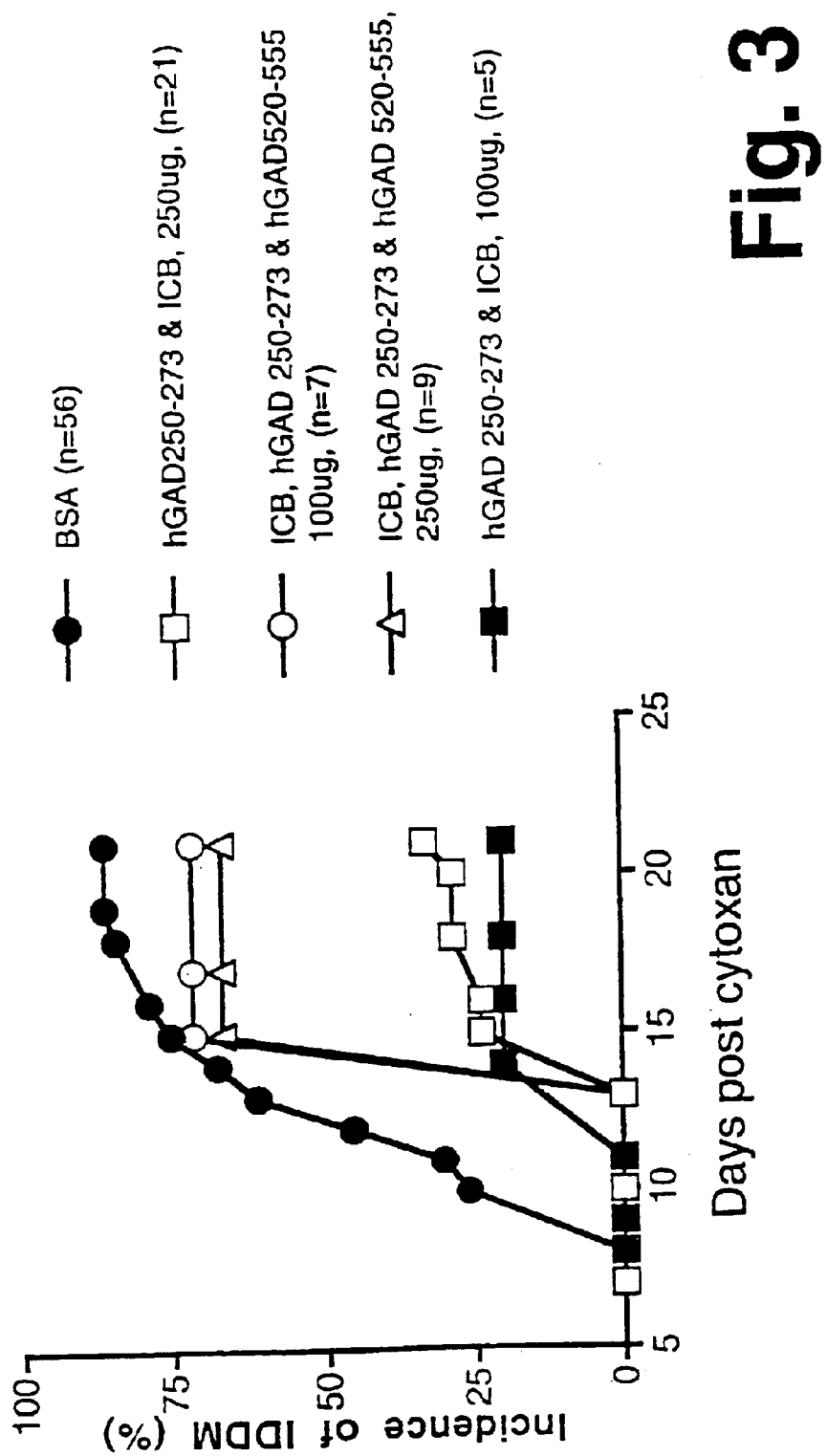
FIG. 3 shows the results of CYTOXAN induced IDDM experiments in which NOD mice were treated with bovine serum albumin (BSA, as control) or the following mixtures of insulin chain B (ICB) and human GAD 65 peptides: 1) 100 μg each of ICB and human GAD 65 peptide 250–273, 2) 250 μg each of ICB and human GAD 65 peptide 250–273, 3) 100 μg each of ICB, human GAD 65 peptide 250–273, and human GAD 65 peptide 520–555, and 4) 250 μg each of ICB, human GAD 65 peptide 250–273, and human GAD 65 peptide 520–555.

Chimeric fusion protein treatment—CYTOXAN model: Groups of randomly selected NOD mice were injected intravenously twice daily with either BSA as a control, or GAD peptides, insulin chain B (ICB) or various combinations of GAD peptides and/or insulin chain B at the doses indicated in the figures on days 1, 3, and 5 following CYTOXAN treatment (day 0). Animals that received injections of BSA (controls) manifested a greater than 80% incidence of diabetes by 21 days following CYTOXAN induction (FIG. 2). In contrast, animals treated with either ICB or either of GAD 65 250–273 or 520–555 peptides, experienced reductions to less than 50% incidence of diabetes. The therapeutic effects of treatment with combinations of ICB and the two GAD peptides were then examined (FIG. 3). Reduction in diabetes incidence to 25% or less was achieved by the combination of GAD 250–273 and ICB at doses of 100 ug or 250 ug per injection.

Figure 4:
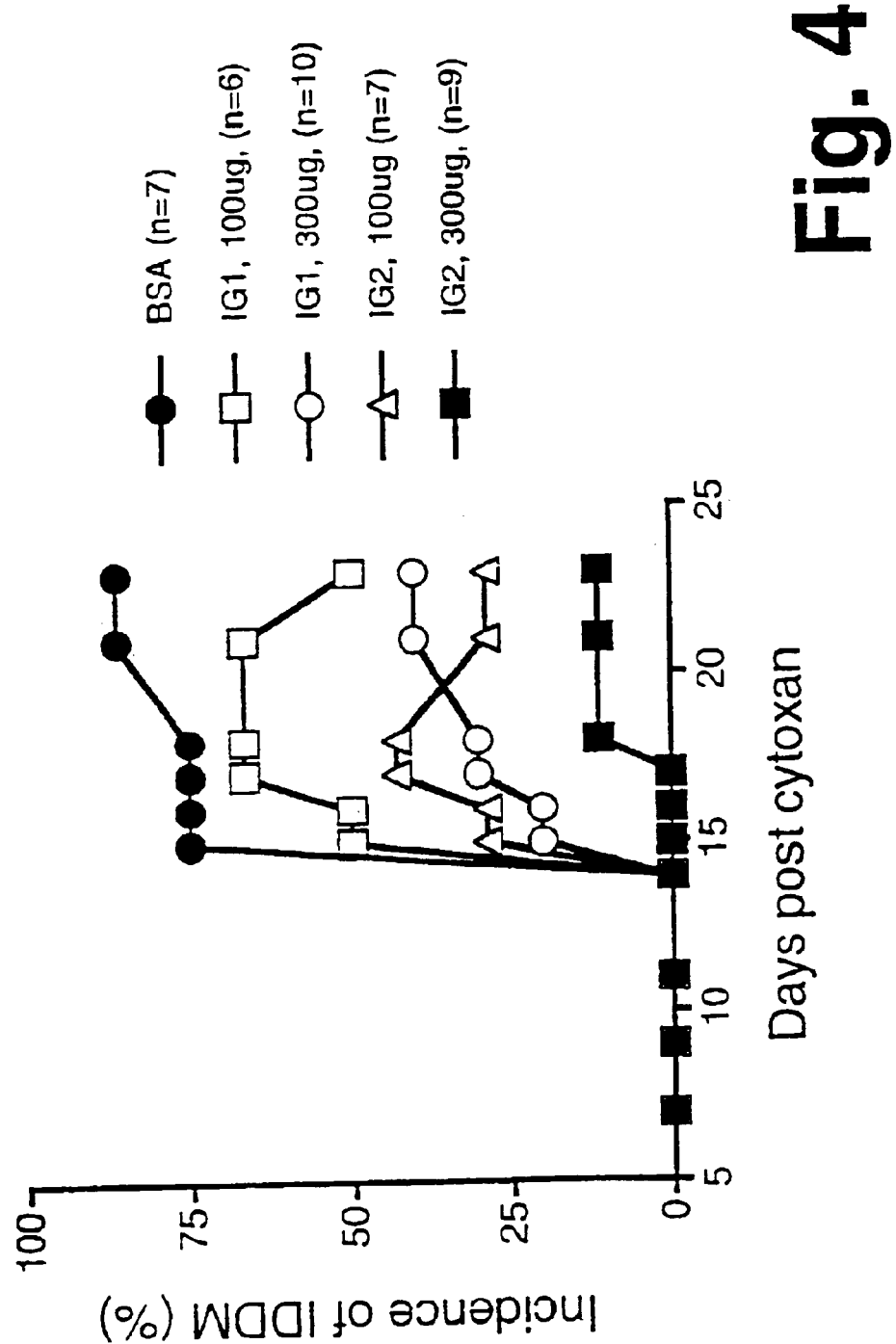
FIG. 4 shows the results of CYTOXAN induced IDDM experiments in which NOD mice were treated with bovine serum albumin (BSA, as control) or 100 μg of the IG1 chimeric protein, 250 μg of the IG1 chimeric protein, 100 μg of the IG2 chimeric protein, or 250 μg of the IG2 chimeric protein.

Surprisingly, the addition of GAD peptide 520–555 (amino acid residues 139–173 of SEQ ID NO:2) appeared to inhibit the therapeutic efficacy of the ICB with GAD 65 250–273 combination. Evaluation in the CYTOXAN model of the IG1 and IG2 chimeric fusion proteins of the invention, showed that treatment with either of these polypeptides mediated a dose-dependent reduction in the incidence of diabetes compared to the BSA treated control animals (FIG. 4). In this experiment, 300 ug doses were more effective than 100 ug doses, and IG2 reduced the incidence of diabetes to a greater degree than IG1. Treatment with 300 ug doses of IG2 reduced disease incidence to less than 12%, compared to greater than 80% disease incidence in the BSA treated control animals.

Chimeric Fusion Protein Treatment—Adoptive Transfer Model:

Diabetogenic splenic mononuclear cells were harvested from newly diabetic NOD mice (onset less than 3 weeks previous). To initiate the destruction of islet beta cells and the development of diabetes, 8–12 week old NOD/SCID mice were injected intravenously with $35 \times 10^6$ diabetogenic spleen cells. The incidence and onset of diabetes were monitored biweekly by urine glucose testing and confirmed by blood glucose testing at the end of the experiment. The average onset time of diabetes after disease induction was approximately 25 days. IV treatment with IG2, IG3, or islet beta cell antigens was initiated on day 3. Animals were treated with 300 ugs of antigen twice daily every other day for a period of six days (from day 3 to day 9, where the time of spleen cell transfer was day 0).

Figure 5:
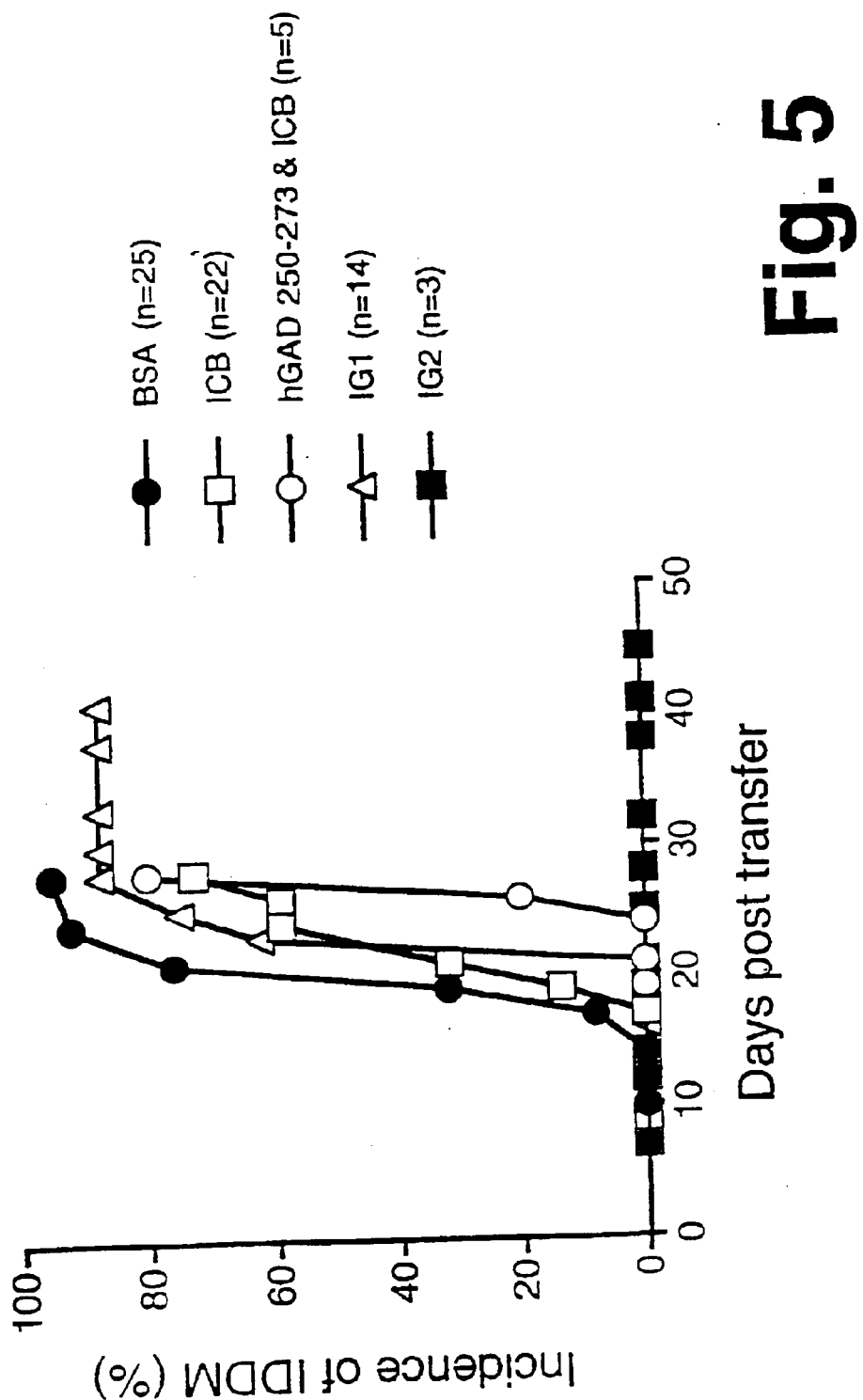
FIG. 5 shows the results of the adoptive transfer of IDDM experiments.
Figure 6:
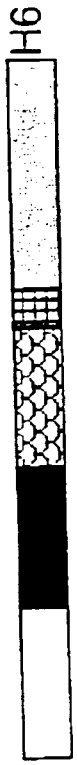
FIG. 6 shows a schematic diagram of the IG4 fusion protein (SEQ ID NO:4). The numbers following the backslashes in the legend indicate the position of the indicated peptide moiety component in native human GAD 65 from which its sequence was derived, while the aa numbers in parentheses the corresponding amino acid numbers in SEQ ID NO:4, and the notation GGG indicates the incorporation at that point of a three glycine helix-breaking linker.
Figure 7:
FIG. 7 shows a schematic diagram of the IG5 fusion protein (SEQ ID NO:5). The numbers following the backslashes in the legend indicate the position of the indicated peptide moiety component in native human GAD 65 from which its sequence was derived, while the aa numbers in parentheses the corresponding amino acid numbers in SEQ ID NO:5, and the notation GGG indicates the incorporation at that point of a three glycine helix-breaking linker.
Figure 8:
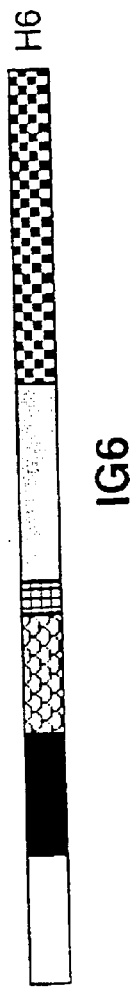
FIG. 8 shows a schematic diagram of the IG6 fusion protein (SEQ ID NO:6). The numbers following the backslashes in the legend indicate the position of the peptide component of the native human protein from which its sequence was derived, while the aa numbers in parentheses the corresponding amino acid numbers in SEQ ID NO:6, and the notation GGG indicates the incorporation at that point of a three glycine helix-breaking linker. As indicated in the legend, IG6 comprises, in addition to the indicated portions of human insulin and human GAD 65 (hGAD 65), a C-terminal portion of human IA-2 (hIA2) spanning amino acids 771–979 of the native human protein (amino acids 176–387 of SEQ ID NO:6), with a three glycine helix-breaking linker incorporated at the N-terminus of this portion of IA-2.
Figure 9:
FIG. 9 shows a schematic diagram of the IG7 fusion protein (SEQ ID NO:7). The numbers following the backslashes in the legend indicate the position of the peptide component of the native human protein from which its sequence was derived, while the aa number in parentheses the corresponding amino acid numbers in SEQ ID NO:7, and the notation GGG indicates the incorporation at that point of a three glycine helix-breaking linker. As indicated in the legend, IG7 comprises, in addition to the indicated portions of human insulin and human GAD 65 (hGAD 65), a C-terminal portion of human IA-2 (hIA2) spanning amino acids 771–979 of the native human protein (amino acids 228–439 of SEQ ID NO:7), with a three glycine helix-breaking linker incorporated at the N-terminus of this portion of IA-2.

The results of these experiments are set forth in FIG. 5. They surprisingly demonstrate that only the IG2 chimeric fusion protein prevented the onset of disease in the NOD/SCID recipients. In contrast, in this model only a slight delay in disease onset was observed in recipients of IG1, insulin chain B (ICB), or the combination of ICB and GAD peptide 250–273. These profound differences in the effects of treatment with IG2 as compared to the other treatment regimens was unexpected. Without wishing to be bound by any particular theory of operation, it is believed that this unexpected finding is a result of the in vivo processing of IG2 into unique antigenic peptides that are particularly effective at eliciting a state of immune tolerance protective against autoimmune diabetes, even in the demanding conditions resulting from challenge with heterogeneous T cell populations derived from the spleens of fully diabetic NOD mice.

Although preferred and other embodiments of the invention have been described herein, further embodiments may be perceived by those skilled in the art without departing from the scope of the invention as defined by the following claims.

REFERENCES

Abbas et. al. 1991. *Cellular and Molecular Immunology* W. B. Saunders Company, Philadelphia.
Ammerer, 1983. *Meth Enzymol* 101:192 et seq.
Atkinson and Maclaren, 1993. *J Clin Invest* 92:1608–1616.
Atkinson et al., 1990. *Lancet* 335:1357–1360.
Atkinson et al., 1990. *Diabetes,* 39:933–937.
Atkinson et al., 1992. *Lancet* 339:458–459.
Atkinson et al., 1993. *J Clin Invest* 91:350–356.
Ausubel et al., 1994. *Current Protocols in Molecular Biology,* John Wiley & Sons, New York.
Baekkeskov et al., 1982. *Nature* 298:167–169.
Baekkeskov et al., 1987. *J Clin Invest* 79:926–934.
Baekkeskov et al., 1990. *Nature* 347:151–156.
Bock et al., 1992. *Lancet* 339:1504–1506.
Boehme and Lenardo 1993. *Eur J Immunol* 23:1552–1560.
Bonifacio et al., 1990. *Lancet* 335:147–149.
Bowman et al., 1994. *Immunol Today* 15(3):115–120.
Brunner et al., 1995. Nature 373:441–444.
Butler et al., 1993. *J Exp Med* 178:2097–2106.
Chang, et al., 1978. *Nature* 275:615 et seq.
Chen et al., 1994. *Science* 265:1237–1240.
Chou, 1990. *Prediction of protein structure and the principles of protein Conformation,* Plenum Press 549–586
Chou and Fasman 1978. *Adv. Enzymol.* 47:45–147.
Cohen et al., 1992. *Ann Rev Immunol* 10:267 et seq.
Coligan et al., 1995. *Current Protocols in Immunology* John Wiley & Sons, New York.
Conrad et al., 1994. *Nature* 371:351–355.
Cotter et al., 1990. *Anticancer Research* 10:1153 et seq.
Crispe 1994. *Immunity* 1:347–349.
Danielet al., 1996. *Proc. Natl. Acad. Sci. USA* 93:956–960.

Davis et al. *Basic Methods in Molecular Biology, 2nd ed.* Appleton and Lange, Norwalk, Conn.
De Aizpurua et al., 1992. *Proc Natl Acad. Sci. USA* 89:9841–9845.
Dhein et al., 1995. *Nature* 373:438–441.
Duvall and Wyllie, 1986. *Immunol Today* 7:115 et seq.
Elliott et al., 1996. *J Clin Invest* 98:1–11.
Evans and Scarpulla, 1989. *Gene* 84:135 et seq.
Farrell, Jr., 1993. *RNA Methodologies: A Laboratory Guide For Isolation And Characterization.* Academic Press Inc., San Diego, Calif.
Foster 1994. in *Harrison's Principles of Int Med*, Thirteenth Ed., McGraw-Hill, N.Y., pp. 1979–2000.
Garnier et al., 1978. *J. Mol. Biol* 120:97–120
Goeddel, et al., 1980. *Nucl Acids Res* 8:4057 et seq.
Griffin and Griffin, Eds., 1994. *PCR Technology, Current Innovations.* CRC Press, Boca Raton, Fla.
Griffin et al, 1995. *Am. J. Pathol* 147:845–857.
Grosjean and Fiers, 1982. *Gene* 18:199 et seq.
Hanninen et al., 1992. *J Clin Invest* 90:1901–1910.
Harrison, 1992. *Immunol Today* 13:348–352.
Harwood, Ed., 1994. *Protocols For Gene Analysis: Methods In Molecular Biology, Vol.* 31. The Humana Press, Totowa, N.J.
Hatfield et al., 1997. *Diabetologia* 40:1327–1333
Hernan et al. 1992 *Biochemistry* 31:8619 et seq.
Herold et al., 1992. *J Exp Med* 176:1107–1114.
Ho et al. 1989. *Gene* 77:51–59.
Honeyman et al., 1993. *J Exp Med* 177:535–540.
Huang and Gorman, 1990. *Mol Cell Biol* 10:1805 et seq.
Ju et al., 1995. *Nature* 373:444–448.
Karjalainen et al., 1992. *New Eng J Med* 327:302–307.
Karounos and Thomas, 1990. *Nature* 39:1085–1090.
Kaufman et al., 1992. *J Clin Invest* 89:283–292.
Kaufman et al., 1993. *Nature* 366:69–72.
Kaufman et al., 1993. *Nature.* 366:69–71.
Kawabe and Ochi, 1991. *Nature* 349:245–248.
Kawasaki et al., 1997. *J. Clin. Endocrinol. Metab.* 82:375–380.
Kerr et al., 1991. *Apoptosis: The Molecular Basis Of Cell Death*, Tomei and Cope (eds.), Cold Spring Harbor Laboratory Press, Plainview, N.Y., pp. 5 et seq.
Kim et al., 1993. *Immunol Invest* 22(3):219–227.
Klaus, ed., 1987. *Lymphocytes: A Practical Approach.* IRL Press, Oxford, England.
Lenardo., 1991. *Nature* 353:858–860.
Lockshin and Zakeri, 1991. *Apoptosis: The Molecular Basis Of Cell Death*, Tomei and Cope (eds.), Cold Spring Harbor Laboratory Press, Plainview, N.Y., pp. 47 et seq.
Lohman et al., 1994. Lancet. 343:1607–1608.
Lohman et al., 1996. J of Autoimmunity. 9:385–389.
Lohmann et al., 1996. *Hormone & Metabolic Res.* 28:357–360.
Luckow, et al., 1988. *Bio/Technology* 6:47 et seq.
Maclaren, et al., PCT patent appl. Int. Pub. No. WO 94/23737.
MacLaren, N and K. Lafferty. 1993. *Diabetes.* 42:1099–1104.
Maniatis, 1982. *Molecular Cloning: A Laboratory Manual.* Cold Spring Harbor Laboratory, Cold Spring Harbor, N.Y.
Marrack and Kappler, 1987. *Science* 238:1073 et seq.
Moir, et al., 1991. *Meth Enzymol* 194:491–507.
Morgenstern and Land, 1990. *Nucl Acids Res* 18:3587 et seq.
Mueller et al., U.S. application Ser. No. 08/482,114, filed Jun. 7, 1995.
Muir, et al., 1995. *J Clin Invest* 95, pp.628–634.
Mullis et al., Eds., 1994. *The Polymerase Chain Reaction.* Springer-Verlag, New York, N.Y.
Nagata and Suda, 1995. *Immunol Today* 16:39 et seq.
Naquet et al., 1988. *J. Immunol.* 140:2569–2578.
Nossal et al., 1992. *Diabetologia*, pp. 549–559.
Ormerod, Ed., 1994. *Flow cytometry: A Practical Approach, 2nd ed.* IRL Press at Oxford University Press, Oxford, England.
Paul, 1989. *Fundamental Immunology. 2nd Ed.* Paul (ed.), Raven Press, New York.
Quinn, A and E. E. Sercarz. 1996. *J. Autoimmunity* 9:365–370.
Ramiya et al., 1996. *J. Autoimmunity* 9:349–356.
*Remington's Pharmaceutical Sciences*, Mack Publishing Co., Philadelphia, Pa., 17th ed. (1985)
Richter et al., 1992. *Proc Natl Acad Sci, USA* 89:8467–8471.
Rudy et al., 1995. *Mol. Medicine* 1:625–633.
Russell et. al. 1993 *Proc Natl Acad Sci USA* 90:4409–4413.
Sambrook et al. 1990. *Molecular Cloning: A Laboratory Manual* Cold Spring Harbor Press, Cold Spring Harbor, N.Y.
Sato et al. 1994. *J Biol Chem* 269:17267 et seq.
Schena, et al., 1991. *Meth Enzymol* 194:389–398.
Schwartz, 1993. Schwartz, RS, "Autoimmunity and Autoimmune Diseases" in Paul, *Fundamental Immunology*, 3rd Ed. Raven Press, New York, 1993, pp. 1033–1097.
Sercarz et. al. 1959. *Nature* 184:1080–1082.
Singer et. al. 1994. *Immunity* 1:365–371.
Smith et al., 1989. *Nature* 337:181–184.
Solimena and De Camilli, 1993. *Nature* 366:15–17.
Steinman, 1995. *Cell* 80:7–10.
Strasser, 1995. *Nature.* 373:385–386.
Studier et al. 1990. *Meth Enzymol* 185:60–89.
Sun et al. 1991. *Eur J Immunol* 21:1461–1468.
Taguchi et al., 1990. *J Immunol Meth* 128:65–73.
Talib, et al., 1991. *Gene* 98:289–293.
Tisch et al, 1993. *Nature.* 366:72–75.
Tisch et al., 1993. *Nature.* 366:72–75.
USP 23/NF 18, 1995 The United States Pharmacopeia/The National Formulary; United States Pharmacopeial Convention, Inc., Rockville, Md.
von Boehmer, 1988. *Ann Rev Immunol* 6:309 et seq.
Walston, et al., 1995. *N Eng J Med* 333:343–347.
Walter et al., 1994. *J. Clin. Invest.* 8:163–166.
Weiner et al., 1997. U.S. Pat. No. 5,643,868.
Weir, 1978. *Handbook of Experimental Immunology, 3rd ed.* Volume 2, Cellular immunology, Blackwell Scientific Publications, Oxford, England.
Wicker et al., 1996. *J. Clin. Invest.* 98:2597–2603.
Williams et al. 1988. *Nucl Acids Res* 16:10453 et seq.
Wong et al., 1998. *J. Clin Invest* 102:947–957.
Xie et al., 1997. *J. Immunol.* 159:3662–3667.
Zhang et al., 1997. *Diabetes* 46:40–43.
Zhang et al., 1991. *Proc Natl Acad. Sci. USA* 88:10252–10256.

TABLE 1

Table-1: dose dependency of cyclophosphamide induced diabetes in non-diabetic male NOD recipients

| CYTOXAN | # Diabetic/Total | % | Mean onset time |
| --- | --- | --- | --- |
| 200 mg/kg | 2/7 | 28.6% | 12 |
| 250 mg/kg | 5/7 | 71.4% | 11 |
| 300 mg/kg | 5/7 | 71.4% | 12.6 |

What is claimed is:

1. A chimeric fusion protein comprising an amino terminus and a carboxyl terminus, wherein the protein comprises, in order, starting at the amino terminus, insulin chain B, insulin chain C and human GAD 65 peptides 115–127, 247–286, and 473–519, wherein the insulin chain B and the at least one human GAD 65 peptide(s) are covalently linked and the chimeric fusion protein is capable of eliciting a human T cell response to insulin chain B and to each of the GAD 65 peptides.

2. A chimeric fusion protein comprising the amino acid sequence spanning amino acid residues 2 to 154 of SEQ ID NO:1.

3. A chimeric fusion protein comprising the amino acid sequence spanning amino acid residues 2 to 174 of SEQ ID NO:2.

4. A chimeric fusion protein comprising the amino acid sequence spanning amino acid residues 2 to 138 of SEQ ID NO:3.

5. A chimeric fusion protein comprising the amino acid sequence spanning amino acid residues 2 to 175 of SEQ ID NO:4.

6. A chimeric fusion protein comprising the amino acid sequence spanning amino acid residues 2 to 226 of SEQ ID NO:5.

7. A chimeric fusion protein comprising the amino acid sequence spanning amino acid residues 2 to 387 of SEQ ID NO:6.

8. A chimeric fusion protein comprising the amino acid sequence spanning amino acid residues 2 to 438 of SEQ ID NO:7.

* * * * *